(12) United States Patent
Lieber et al.

(10) Patent No.: US 11,067,534 B2
(45) Date of Patent: *Jul. 20, 2021

(54) MULTI-CHANNEL NANOPORE SENSING BY LOCAL ELECTRICAL POTENTIAL MEASUREMENT

(71) Applicant: President and Fellows of Harvard College, Cambridge, MA (US)

(72) Inventors: Charles M. Lieber, Lexington, MA (US); Ping Xie, Needham, MA (US)

(73) Assignee: President and Fellows of Harvard College

( * ) Notice: Subject to any disclaimer, the term of this patent is extended or adjusted under 35 U.S.C. 154(b) by 26 days.

This patent is subject to a terminal disclaimer.

(21) Appl. No.: 16/554,753

(22) Filed: Aug. 29, 2019

(65) Prior Publication Data

US 2019/0391112 A1 Dec. 26, 2019

Related U.S. Application Data

(63) Continuation of application No. 15/616,225, filed on Jun. 7, 2017, now Pat. No. 10,436,747, which is a
(Continued)

(51) Int. Cl.
*G01N 27/447* (2006.01)
*B82Y 30/00* (2011.01)
(Continued)

(52) U.S. Cl.
CPC ............ *G01N 27/447* (2013.01); *B82Y 30/00* (2013.01); *C12Q 1/6869* (2013.01); *G01N 33/48721* (2013.01); *B82Y 15/00* (2013.01)

(58) Field of Classification Search
CPC .............................................. G01N 33/48721
See application file for complete search history.

(56) References Cited

U.S. PATENT DOCUMENTS 7,468,271 B2 12/2008 Golovchenko et al.
8,652,779 B2 2/2014 Turner et al.
(Continued)

FOREIGN PATENT DOCUMENTS

CN 101668866 A 3/2010
EP 1657539 A1 5/2006
(Continued)

OTHER PUBLICATIONS

PCT/US2011/034426, International Search Report, Form PCT/ISA/210 first sheet, second sheet, continuation of second sheet, and patent family annex, dated Oct. 2012.
(Continued)

*Primary Examiner* — Alexander S Noguerola
(74) *Attorney, Agent, or Firm* — Theresa Lober

(57) ABSTRACT

There is provided a multi-channel nanopore sensor having a plurality of independent nanopore sensors. Each independent nanopore sensor includes a nanopore disposed in a support structure. A fluidic connection is between a first fluidic reservoir, common to all of the independent nanopore sensors, and an inlet to the nanopore, with a first ionic solution of a first ionic concentration disposed in the first fluidic reservoir. A fluidic connection is between a second fluidic reservoir, common to all of the independent nanopore sensors, and an outlet from the nanopore, with a second ionic solution of a second ionic concentration, different than the first ionic concentration, disposed in the second fluidic reservoir. An electrical transduction element, disposed in contact with that ionic solution having a lower ionic concentration, is arranged at a site that produces an electrical signal indicative of electrical potential local to that ionic solution having a lower ionic concentration.

39 Claims, 24 Drawing Sheets

Related U.S. Application Data continuation of application No. 14/009,348, filed as application No. PCT/US2011/034426 on Apr. 29, 2011, now Pat. No. 9,702,849.

(60) Provisional application No. 61/471,345, filed on Apr. 4, 2011.

(51) Int. Cl.
*C12Q 1/6869* (2018.01)
*G01N 33/487* (2006.01)
*B82Y 15/00* (2011.01)

(56) References Cited

U.S. PATENT DOCUMENTS

| | | | |
|---|---|---|---|
| 8,901,914 | B2 | 12/2014 | Fraikin et al. |
| 8,986,928 | B2 | 3/2015 | Turner et al. |
| 8,993,234 | B2 | 3/2015 | Turner et al. |
| 9,017,937 | B1 | 4/2015 | Turner et al. |
| 9,702,849 | B2 * | 7/2017 | Lieber .................. B82Y 30/00 |
| 2006/0063171 | A1 | 3/2006 | Akeson et al. |
| 2006/0073489 | A1 * | 4/2006 | Li ........................ B01D 57/02 435/6.11 |
| 2006/0275779 | A1 * | 12/2006 | Li .......................... B82Y 5/00 435/6.11 |
| 2007/0178507 | A1 | 8/2007 | Wu et al. |
| 2008/0171316 | A1 | 7/2008 | Golovchenko et al. |
| 2009/0136958 | A1 * | 5/2009 | Gershow ............. C12Q 1/6869 435/6.13 |
| 2010/0066348 | A1 | 3/2010 | Merz et al. |
| 2010/0243449 | A1 * | 9/2010 | Oliver ................. C12Q 1/6874 204/450 |
| 2010/0304980 | A1 | 12/2010 | Takeuchi et al. |
| 2010/0331194 | A1 | 12/2010 | Turner et al. |
| 2011/0053284 | A1 | 3/2011 | Meller et al. |

FOREIGN PATENT DOCUMENTS

| | | | |
|---|---|---|---|
| WO | 2009035647 | A1 | 3/2009 |
| WO | 2010020912 | A1 | 2/2010 |
| WO | 2010111605 | A2 | 9/2010 |
| WO | 2010117470 | A2 | 10/2010 |
| WO | 2011027379 | A1 | 3/2011 |

OTHER PUBLICATIONS

PCT/US2011/034426, Written Opinion of the International Searching Authority, PCT/ISA/237 cover sheet, sheets for Box I, Box V, and Box VIII, and separate sheet sheets 1-4,Oct. 2013.
European Patent Application No. 11720230.9-1554, EPO Communication Pursuant to Rules 161(1) and 162 EPC. p. 1-2, WO p. 1-7, claims 44-50, Nov. 2013.
European Patent Application No. 11720230.9-1554, Response to EPO Communication, pp. 1-9, clean copy of claims pp. 1-4, marked-up copy of claims pp. 1-7, May 2014.
Chinese Patent Appl. No. 201180071394.4, First CN Office Action text pp. 1-5, First Office Action pp. 1-4, Search Report pp. 1-2, Dec. 2014.
Chinese Patent Appl. No. 201180071394.4, Response to First CN Office Action and claim amendments, pp. 1-16, Jun. 2015.
Chinese Patent Appl. No. 201180071394.4, Second CN Office Action pp. 1-3, Text of Second Office Action pp. 1-8, Oct. 2015.
Chinese Patent Appl. No. 201180071394.4, Response to Second CN Office Action pp. 1-8, Feb. 2016.
Chinese Patent Appl. No. 201180071394.4, Third CN Office Action pp. 1-3, Text of Third Office Action pp. 1-6, Jul. 2016.
Chinese Patent Appl. No. 201180071394.4, Response to Third CN Office Action and claim amendments, pp. 1-16, Oct. 2016.
Lee et al., "The Effect of Axial Concentration Gradient on Electrophoretic Motion of a Charged Spherical Particle in a Nanopore," Microgravity Sci. Technol., vol. 22, pp. 329-338, Apr. 24, 2010.
Wanunu et al., "Electrostatic focusing of unlabelled DNA into nanoscale pores using a salt gradient," nature nanotechnology, vol. 5, pp. 160-165, Dec. 2009.
Ivanov et al., "DNA TUnneling Detector Embedded in a Nanopore," Nano Lett., vol. 11, No. 1, pp. 279-285, Dec. 2010.
Xie et al., Nanowire-nanopore FET sensor for DNA detection, Slides 1-24, Nanobiophysics in the 21st Centure, Brown University, Providence, RI, Oct. 30, 2010.
Xie et al., "Nanowire-nanopore FET sensors for DNA detection during translocation," Slides 1-20, presented at APS Mar. Meeting 2011, vol. 56, No. 1, Dallas, Texas, Mar. 21-25, 2011.
Zwolak, "Colloquium: Physical approaches to DNA sequencing and detection," Rev. Mod. Phys., vol. 80, No. 1 pp. 141-165, Jan.-Mar. 2008.
Clarke et al., "Continuous base identification for single-molecule nanopore DNA sequencing," nature nanotechnology, vol. 4, pp. 265-270, Apr. 2009.
Kastner, "The single-electron transistor," Rev. Mod. Phys., vol. 64, No. 3, pp. 849-858 and figure sheet, Jul. 1992.
Mali et al., "The dnaSET: A Novel Device for Single-Molecule DNA Sequencing," IEEE Trans. Elect. Dev., vol. 51, No. 12, pp. 2004-2012, Dec. 2004.
Chinese Patent Application No. 201810026232.2, First CN Office Action: Letter with English language report from CN associate, pp. 1-5, listing of pending claims, pp. 1-3, CN Office Action English Language version, pp. 1-4, English language translation of text of First Action, pp. 1-4, CN Search Report pp. 1-3, dated Apr. 18, 2019.
Chinese Patent Application No. 201810026232.2, Response to First CN Office Action, pp. 1-9, dated Jul. 16, 2019.
European Patent Application No. 11720230.9-1020, EPO Communication Pursuant to Article 94(3) EPC, pp. 1-2, Form 2906 Reasons Sheets 1-5, Aug. 2019.
European Patent Application No. 11720230.9-1020, Response to EPO Communication Pursuant to Article 94(3) EPC, pp. 1-5, Claim amendments pp. 1-4, Specification Amendments pp. 1, 2, 3a, 5, 6, 12, 43, Dec. 2019.
Chinese Patent Application No. 201810026232.2, Second CN Office Action: Letter with English language report from CN associate, pp. 1-3, Sep. 2019.
Chinese Patent Application No. 201810026232.2, Response to Second CN Office Action: Listing of claim amendments, pp. 1-4, Jan. 2020.

* cited by examiner

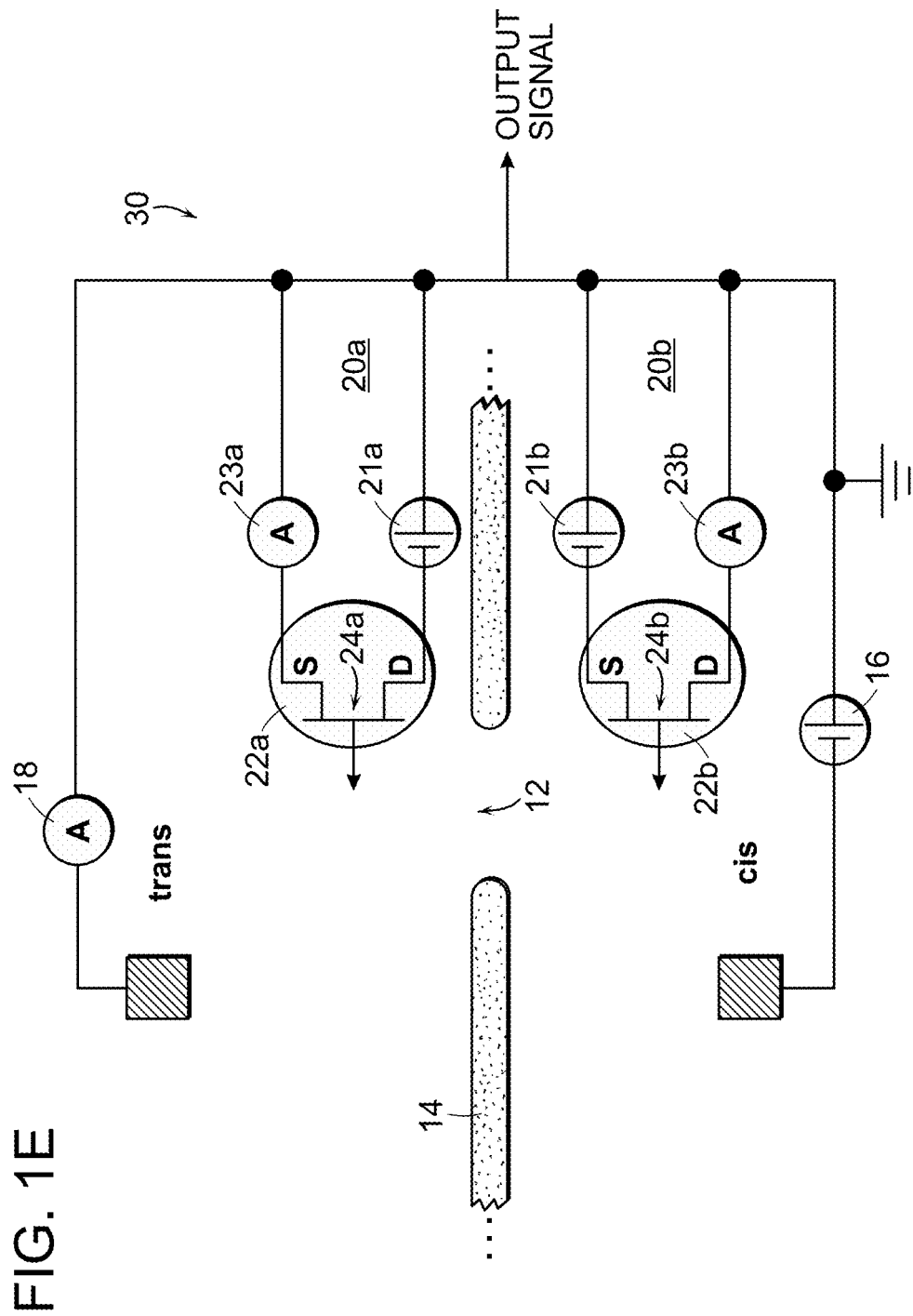

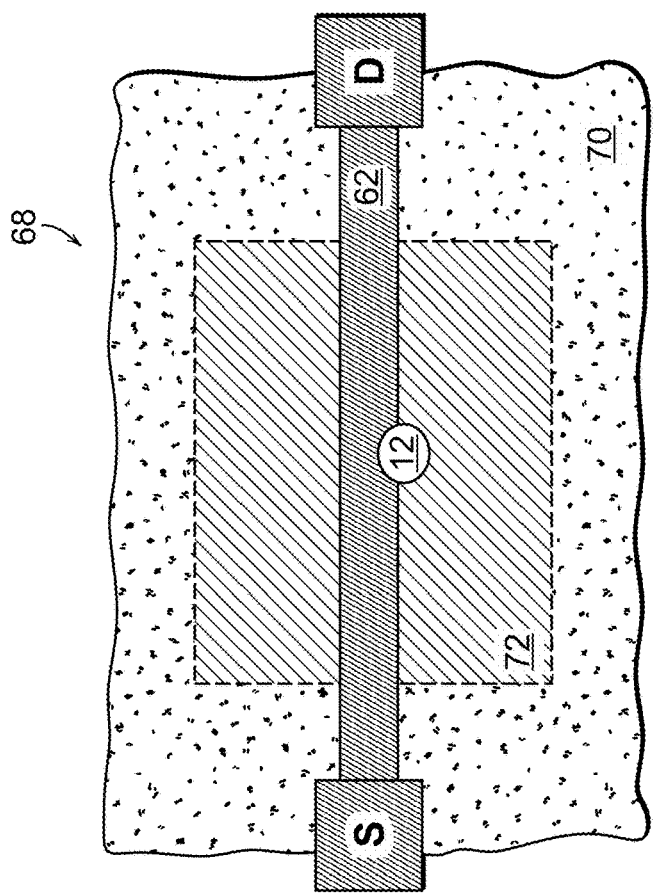
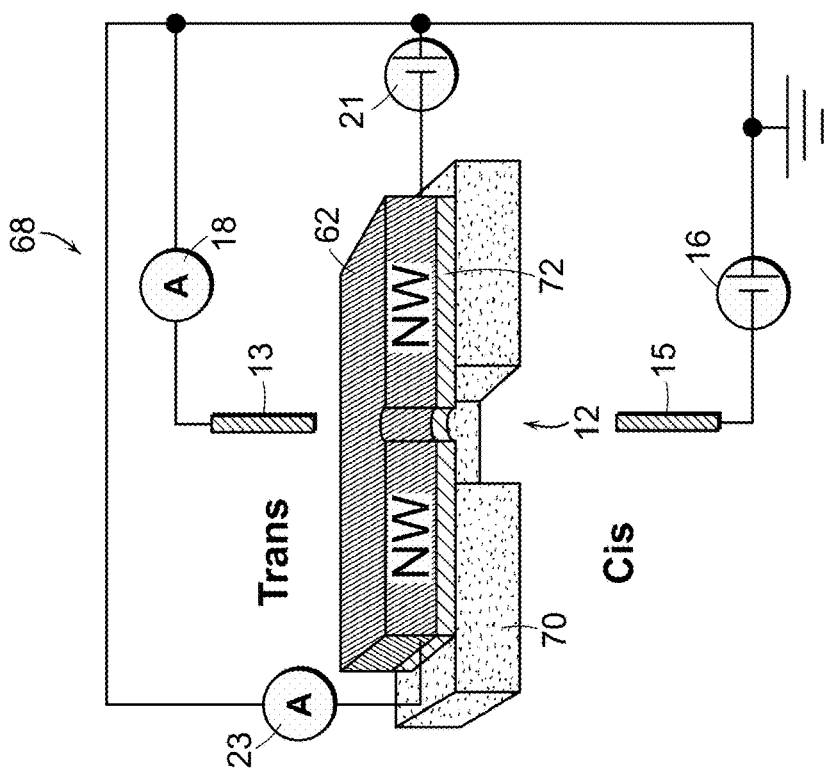
FIG. 7A
FIG. 7B

MULTI-CHANNEL NANOPORE SENSING BY LOCAL ELECTRICAL POTENTIAL MEASUREMENT

CROSS-REFERENCE TO RELATED APPLICATIONS

This application is a continuation of copending application Ser. No. 15/616,225, filed Jun. 7, 2017, which is a continuation of application Ser. No. 14/009,348, filed Oct. 2, 2013, now issued as U.S. Pat. No. 9,702,849, which is the National Stage of International Application No. PCT/US11/034426, filed Apr. 29, 2011, which claims the benefit of U.S. Provisional Application No. 61/471,345, filed Apr. 4, 2011, the entirety of all which is hereby incorporated by reference.

STATEMENT REGARDING FEDERALLY SPONSORED RESEARCH

This invention was made with Government support under Contract No. 5DP1OD003900 awarded by the National Institute of Health. The Government has certain rights in the invention.

BACKGROUND

This invention relates generally to sensing systems that employ a nanopore sensor, and more particularly relates to techniques for sensing species as the species translocate through a nanopore sensor.

Solid state and biological nanopores are increasingly the focus of considerable effort towards the development of a low cost, high throughput sensing system that can be employed for sensing a wide range of species, including single molecules. For example, there is has been proposed the use of solid state nanopores for enabling single-molecule DNA sequencing technology. While single DNA bases produced by enzymatic cleavage of DNA have been detected and differentiated using modified protein nanopores, the goal of sequencing a single-stranded DNA (ssDNA) molecule by translocation of the molecule through a nanopore has not yet been fully realized.

One proposed approach for nanopore sensing is based on a method in which there is detected a modulation of ionic current passing through a nanopore that is disposed in a membrane or other support structure. Given a molecule that is provided in an ionic solution to be translocated through a nanopore, as the molecule translocates through the nanopore, the ionic current that passes through the nanopore is correspondingly decreased from the ionic current passing through the nanopore without a molecule. This nanopore sensing approach is limited in that it is in general quite difficult to record the small picoampere ionic current signals that are characteristic of molecular nanopore translocation at a bandwidth that is consistent with very fast molecular translocation speeds. The speed of a DNA molecule translocation through a nanopore can be ~1 μs/nucleotide. Furthermore, the recording of such small current signals at high bandwidth in a parallel multiplexed format has been shown to be extremely difficult.

To circumvent the technical challenges of the ionic current measurement method for nanopore sensing, several alternative nanopore sensing methods have been proposed. Such alternative methods can be generalized as directed to an effort to record larger and relatively more-local nanopore signals employing electronic sensors that are integrated with the nanopore. These nanopore sensing methods include, e.g., measurement of capacitive coupling across a nanopore and tunnelling current measurements through a species translocating a nanopore. While providing interesting alternative sensing techniques, such capacitive coupling and tunnelling current measurement techniques have not yet improved upon the conventional ionic current detection technique for nanopore sensing, and ionic current detection techniques remain challenged by signal amplitude and signal bandwidth issues.

SUMMARY OF THE INVENTION

There is provided a multi-channel nanopore sensor that overcomes the measurement sensitivity and signal bandwidth limitations of conventional nanopore sensors and nanopore sensing techniques by employing a multi-channel structure that enables local electrical potential sensing. The multi-channel nanopore sensor includes a plurality of independent nanopore sensors. Each independent nanopore sensor in the plurality of independent nanopore sensors includes a nanopore disposed in a support structure. A fluidic connection is disposed between a first fluidic reservoir, common to all of the independent nanopore sensors, and an inlet to the nanopore, with a first ionic solution of a first ionic concentration disposed in the first fluidic reservoir. A fluidic connection is disposed likewise between a second fluidic reservoir, common to all of the independent nanopore sensors, and an outlet from the nanopore, with a second ionic solution of a second ionic concentration, different than the first ionic concentration, disposed in the second fluidic reservoir. Each independent nanopore sensor includes an electrical transduction element that is disposed in contact with that ionic solution, of the first and second ionic solutions, which has a lower ionic concentration, having a lower ionic concentration. The electrical transduction element is arranged at a site that produces in the electrical transduction element an electrical signal indicative of electrical potential local to that ionic solution having a lower ionic concentration.

This multi-channel nanopore sensor arrangement enables local electrical potential sensing with high sensitivity, high bandwidth, and large signal differentiation between differing objects translocating through each nanopore in the plurality of independent nanopore sensors. Each independent nanopore sensor operates independently even with integration into a single multi-channel nanopore sensor. As a result, high-through put nanopore sensing applications, such as DNA sequencing, can be accomplished both efficiently and precisely with the multi-channel nanopore sensor. Other features and advantages will be apparent from the following description and accompanying figures, and from the claims.

BRIEF DESCRIPTION OF THE DRAWINGS

FIG. 1E is a circuit diagram of an example transistor implementation of a combination of the sensor configurations of FIGS. 1A and 1C;

FIGS. 7A-7B are a schematic view of a nanopore sensor configured for local electrical potential measurement with a nanowire FET disposed on a graphene membrane, and a plan view of an example implementation of this nanopore sensor, respectively;

DETAILED DESCRIPTION

Figure 1A:
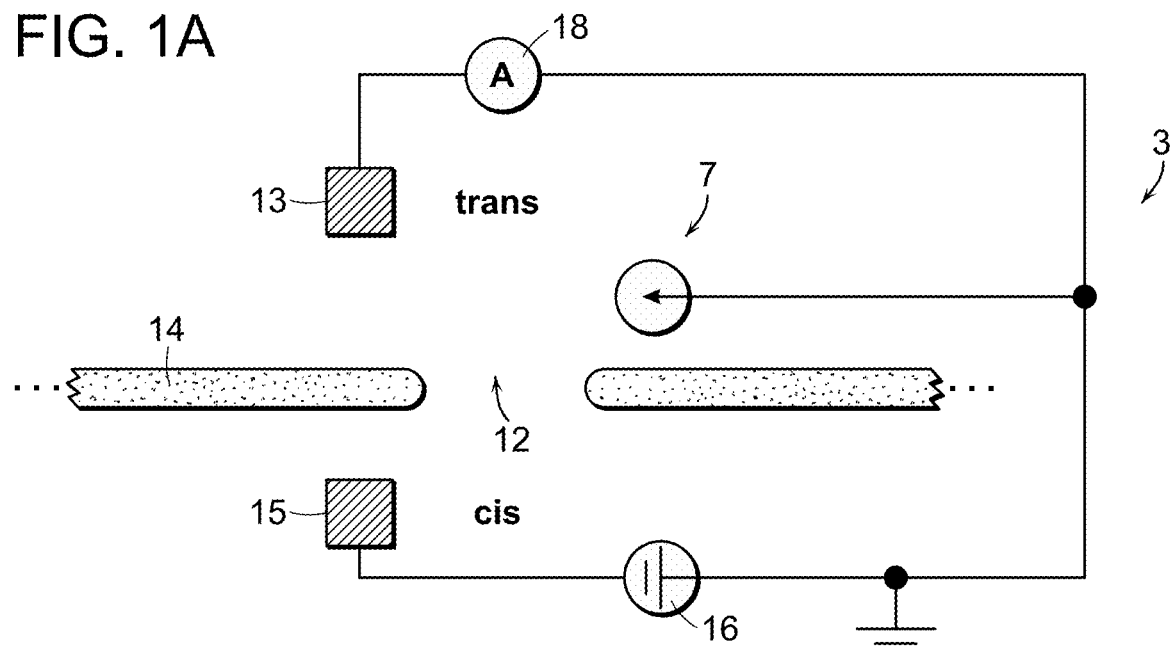
FIG. 1A is a schematic circuit diagram of a first example nanopore sensor configuration for measuring local electrical potential.

FIGS. 1A-1E are schematic views of example nanopore sensor configurations that enable a local electrical potential sensing method for nanopore sensing. For clarity of discussion, device features illustrated in the figures are not shown to scale. Referring to FIG. 1A, there is shown a nanopore sensor 3 including a support structure, such as a membrane 14, in which is disposed a nanopore 12. The nanopore 12 is configured in the support structure between two fluidic reservoirs shown here schematically as a trans reservoir and a cis reservoir such that the nanopore 12 is the only path of fluidic communication between the cis and trans reservoirs. One reservoir is connected to an inlet to the nanopore while the other reservoir is connected to an outlet from the nanopore. In operation of the nanopore sensor for local electrical potential measurement detection of species translocation through the nanopore, one or more objects of a species, such as molecules, are provided in a fluidic solution in one of the reservoirs for translocation through the nanopore to the other of the two reservoirs. For many applications, and in particular for molecular sensing applications, it can be preferred to provide the molecules or other species objects in an ionic fluidic solution in one of the reservoirs.

The nanopore is provided as an aperture, gap, or other hole in the support structure and is provided with an extent, or for corresponding the geometry, a diameter, that is suitable for sensing species objects of interest. For example, for sensing molecular nanopore translocation, a nanopore of less than about 100 nm can be preferred, and a nanopore of less than 10 nm, 5 nm, or 2 nm can be more preferred. As discussed below, a nanopore of even 1 nm can be suitable and even preferred for some molecular sensing applications.

The reservoirs or other components of the nanopore sensor are configured to provide a driving force for moving objects of a species, such as molecules, through the nanopore from one of the reservoirs to the other of the reservoirs. For example, electrodes 13, 15 can be provided in a circuit with voltage and current elements 16, 18 to produce an electrophoretic force between the reservoirs for electrophoretically driving a fluidic solution, such as an electrically conductive ionic solution, and the species in the solution, through the nanopore from one reservoir to the other reservoir. To enable electrophoretic driving of the species through the nanopore, the fluidic solutions of the reservoirs can be provided as electrically conductive ionic solutions having pH and other characteristics that are amenable to the species in the solution. Thereby an electrical circuit can be connected with the reservoir solutions in series through the nanopore, with electrodes 13, 15 as shown in the figures, providing an electrical voltage bias between the solutions, across the nanopore.

As shown in FIG. 1A, there can be provided in the nanopore sensor a transduction element that senses the electrical potential local to the site of the element and that develops a characteristic that is indicative of that local electrical potential. For example, an electrical connection, such as device or region of a device and/or circuit 7, a wire, or combination of circuit elements, that senses the electrical potential local to the site of the device and/or circuit 7 can be provided, to develop a signal indicative of local electrical potential. The location of the electrical potential sensing can be in a reservoir, on a surface of the support structure, or other location within the nanopore sensor.

Figure 1C:
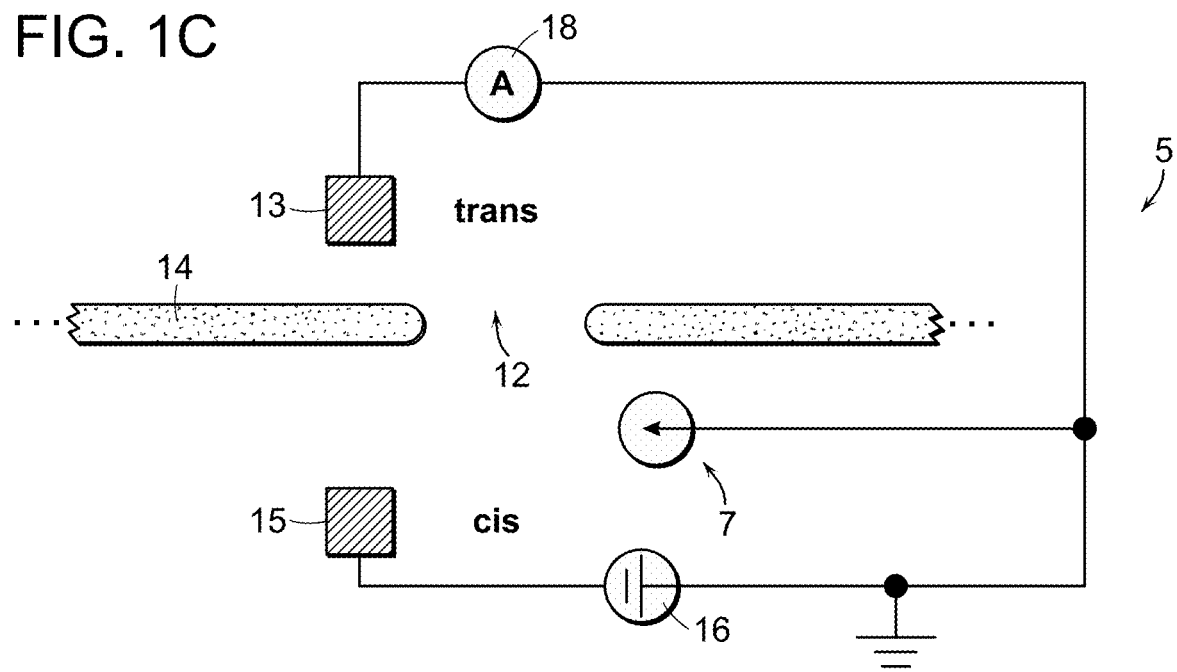
FIG. 1C is a schematic circuit diagram of a second example nanopore sensor configuration for measuring a local electrical potential.
Figure 1B:
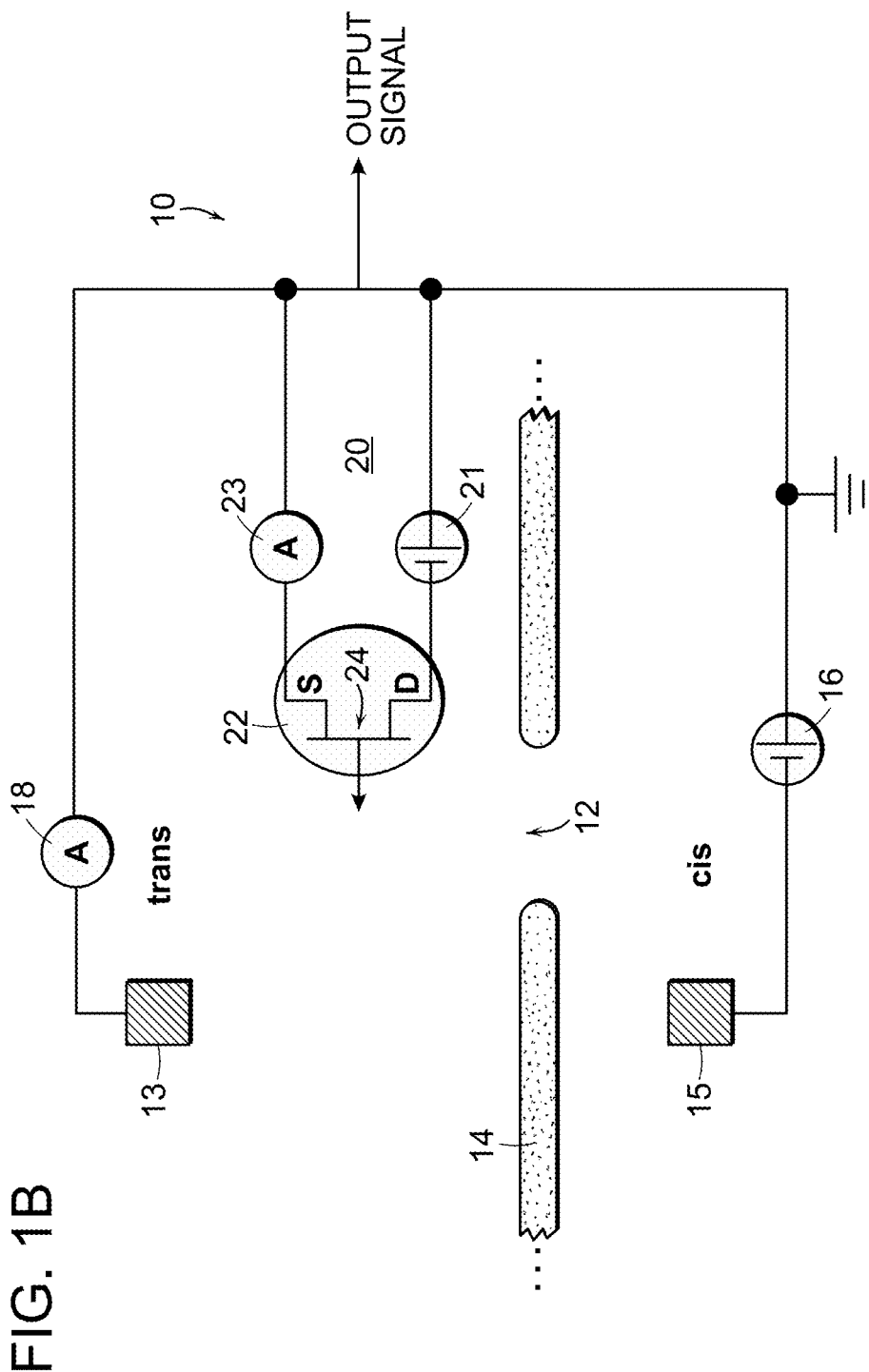
FIG. 1B is a circuit diagram of an example transistor implementation of the nanopore sensor configuration of FIG. 1A.

For example, as shown in FIG. 1B, there can be provided a circuit 20 that includes, e.g., a transistor device 22, having a source, S, a drain, D, and a channel region 24. The channel region 24 is in this example physically disposed at a location in the nanopore sensor environment at which a local electrical potential measurement is to be made. This physical location of the channel region 24 of the transistor can be at any convenient and suitable site for accessing local electrical potential.

Figure 1D:
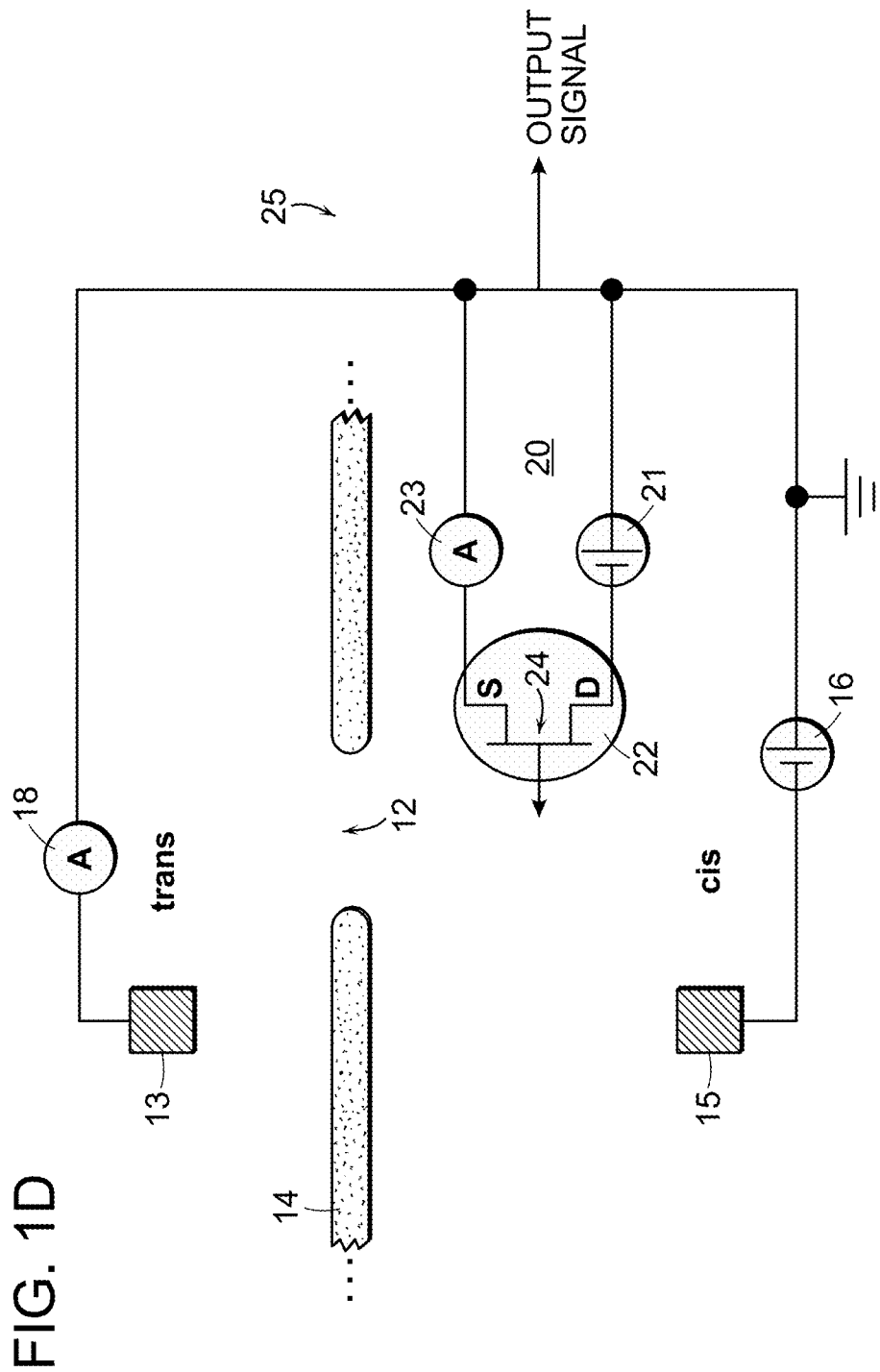
FIG. 1D is circuit diagram of an example transistor implementation of the nanopore sensor configuration of FIG. 1C.

In the example arrangements of FIGS. 1A-1B, an electrical potential sensing circuit is configured local to the trans reservoir to provide a transistor or other device that measures the electrical potential local to the trans reservoir at the trans reservoir-side of the nanopore 12. Alternatively, as shown in FIG. 1C, an electrical potential sensing device or circuit 7 can be configured at the cis reservoir side of the nanopore. Here, e.g., as shown in FIG. 1D, there can be provided a circuit including a transistor 24 or other device for measuring electrical potential local to the cis reservoir at the cis reservoir side of the nanopore 12.

In a further example alternative configuration, as shown in FIG. 1E, there can be included two or more circuits 20a, 20b, etc., with, e.g., transistors 22a, 22b that sense the electrical potential at two or more locations in the nanopore sensor system, such as each side of the nanopore membrane. Depending on the physical implementation of the electrical potential sensing circuit, the electrical potential at the two sides of the nanopore membrane 14 can thereby be measured with this arrangement. This is an example configuration in which is enabled a measurement of the difference in local potential between two sites in the nanopore sensor. It is therefore intended that the term "measured local electrical potential" refer to the potential at a single site in the nanopore sensor, refer to a difference or sum in local electrical potential between two or more sites, and refer to a local potential at two or more sites in the nanopore sensor configuration.

Figure 1F:
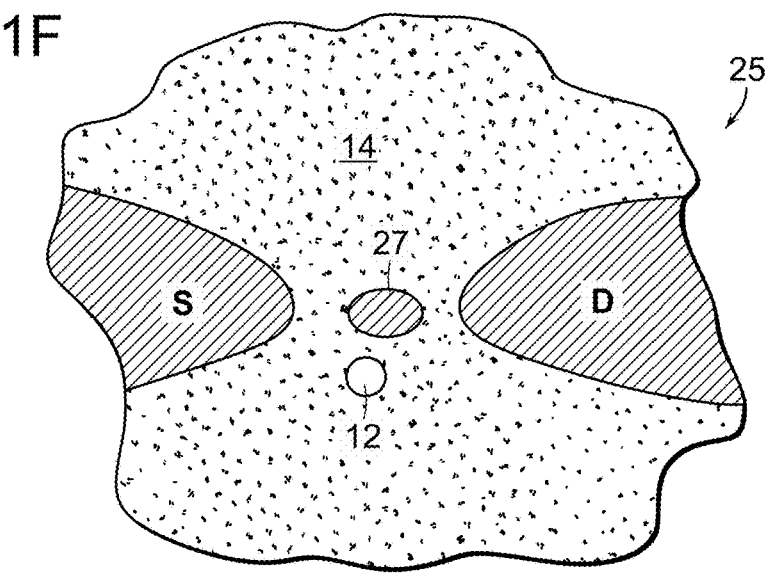
FIG. 1F is a schematic plan view of a single electron transistor implementation of a nanopore sensor configuration for measuring local electrical potential.

The local electrical potential measurement can be made by any suitable device and/or circuit or other transduction element, including biological or other non-solid state transduction elements, and is not limited to the transistor implementation described above. For example, as shown in FIG. 1F, there can be provided on the membrane 14 or other support structure a single electron transistor (SET) circuit 27. The source, S, and drain, D, regions of the SET are disposed on the membrane or other support structure, providing tunneling barriers to the SET 27. In the resulting quantum dot system, the electrical conductance through the SET 27 depends on the energy level of the SET with respect to the Fermi level of the source, S, and drain, D. With the nanopore 12 located in the vicinity of the SET, the electrical potential, and corresponding energy level, of the SET changes as species objects translocate through the nanopore, changing the conductance of the SET circuit.

Figure 1G:
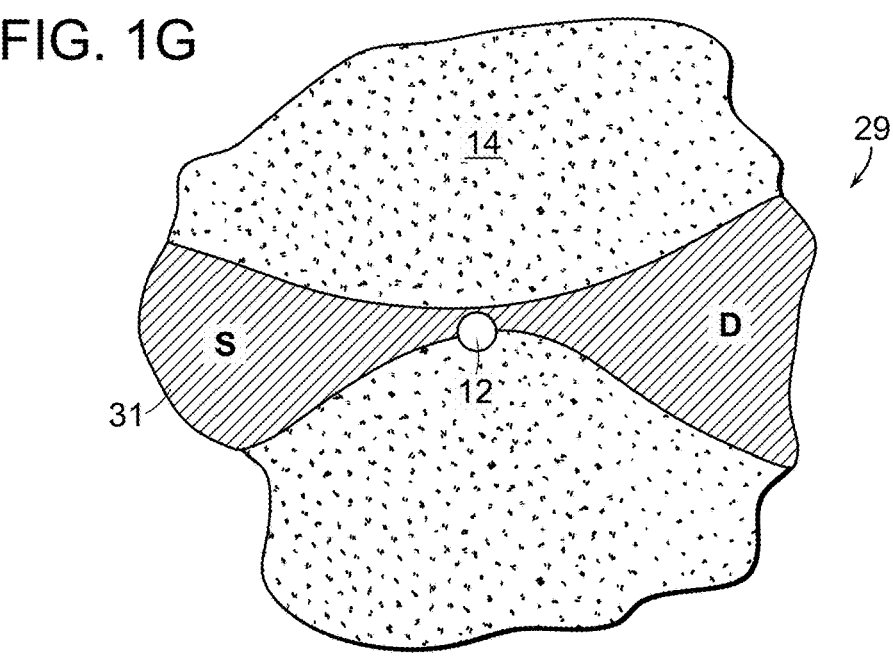
FIG. 1G is a schematic plan view of a quantum point contact implementation of a nanopore sensor configuration for measuring local electrical potential.

In a further example, as shown in FIG. 1G, there can be provided on the membrane 14 or other structure a quantum point contact (QPC) system 29 for making a local electrical potential measurement. In this system, an electrically conductive region 31 is provided that forms source, S, and drain, D, regions that are connected via a very thin conducting channel region at the site of the nanopore 12. The channel region is sufficiently thin that the electronic carrier particle energy states that are perpendicular to the channel region are quantized. As species objects translocate through the nanopore, the Fermi level inside the thin conduction channel region changes, resulting in a change in the number of quantized states below the Fermi level, and a corresponding change in QPC conductance.

Figure 1H:
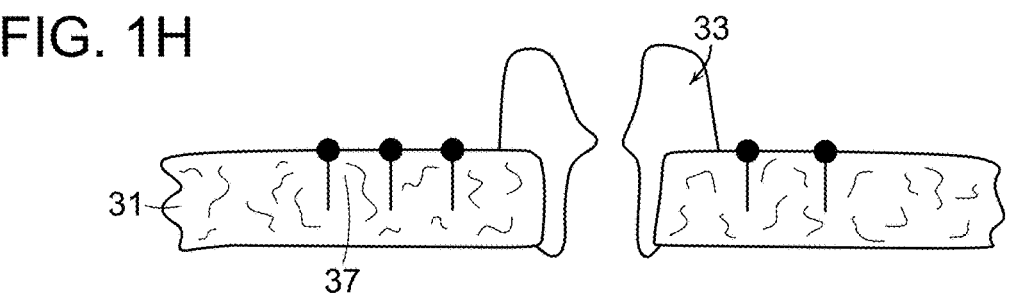
FIG. 1H is a schematic side view of a lipid bilayer including fluorescent dye arranged for implementation of a protein nanopore sensor configuration for measuring local electrical potential.

Accordingly, the nanopore sensor is not limited to solid state nanopore configurations with solid state voltage sensing devices. Biological nanopores and potential sensing arrangements can also be employed, e.g., with a protein nanopore or other suitable configuration. For example, as shown in FIG. 1H, there can be provided a lipid bilayer membrane 31 in which is disposed a protein nanopore 33. A voltage-sensitive dye, e.g., a fluorescent direct dye 37, is provided in the lipid bilayer. With this arrangement, when a species object such as a molecule or polymer translocates through the protein nanopore, the voltage drop across the lipid bilayer changes, and the fluorescence of the dye is modulated by the voltage change. Optical detection or sensing of the dye fluorescence and changes to that fluorescence provide sensing of the potential at the membrane location. Optical microscope or other arrangement can be employed for making this potential measurement as an optical output signal from the nanopore sensor.

This lipid bilayer nanopore sensor is an example of a biological nanopore sensor that is based on sensing of the local potential at the site of the nanopore. The method of local potential measurement for nanopore translocation detection is not limited to a particular solid state or biological configuration and can be applied to any suitable nanopore configuration.

Figure 2A:
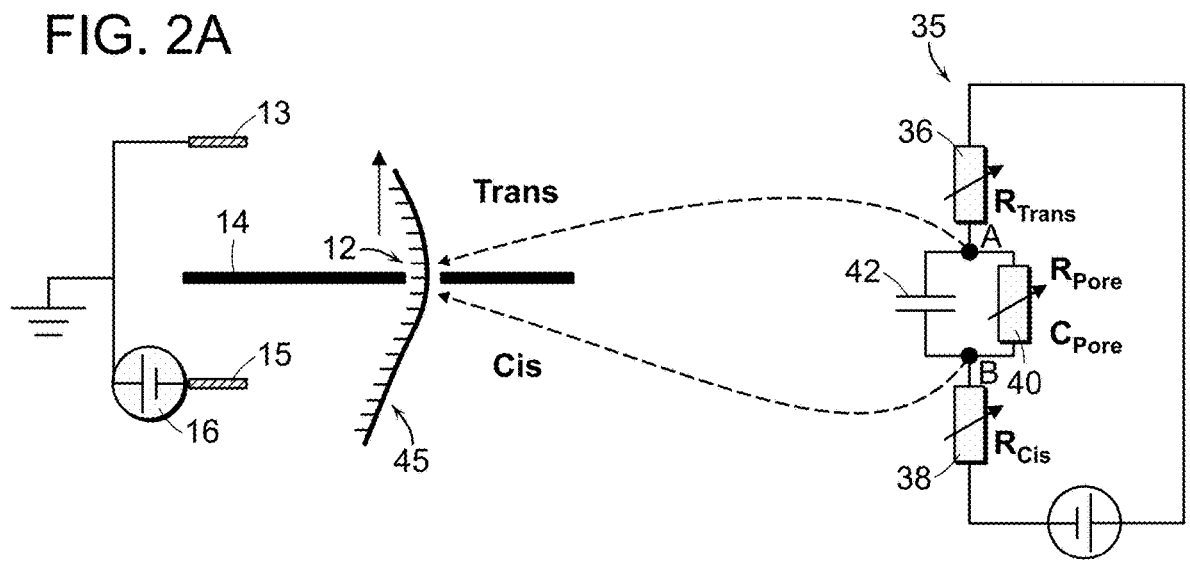
FIG. 2A is a schematic diagram and corresponding circuit elements for a nanopore sensor configuration for measuring local electrical potential.

Referring to FIG. 2A, these configurations for measuring the local electrical potential at one or more sites in a nanopore sensor can be employed in a method for sensing the translocation of species through the nanopore. To explain the principle of this sensing, it is instructive to model the nanopore sensor as a circuit 35 including electrical components corresponding to physical elements of the sensor, as shown in FIG. 2A. The cis and trans reservoirs can each be modeled with a characteristic fluidic access resistance, $R_{Trans}$, 36, $R_{Cis}$, 38. This access resistance is the fluidic resistance from the bulk of the reservoir solution to the site of the nanopore. The nanopore can be modeled with a characteristic nanopore solution resistance, $R_{Pore}$, that is the fluidic resistance of solution through the length of the nanopore between the two sides of the membrane or other structure in which the nanopore is disposed. The nanopore can also be modeled with a characteristic capacitance $C_{Pore}$, that is a function of the membrane or other support structure in which the nanopore is disposed. The access resistance of both chambers and the nanopore solution resistance 40 are variable.

In a nanopore sensor starting condition in which no species are translocating through the nanopore, the nanopore can be characterized by the solution resistance, $R_{pore}$, given above, and both fluidic reservoirs can be characterized by the access resistances of the trans reservoir and the cis reservoir, $R_{Trans}$ and $R_{Cis}$, respectively. Then when a species object, such as a biological molecule 45, translocates through the nanopore 12 as shown in FIG. 2A, the solution resistance, $R_{Pore}$, of the nanopore and the access resistances, $R_{Trans}$ and $R_{Cis}$, of each of the reservoirs, change because the molecule in the nanopore at least partially blocks the passageway through the nanopore length, changing the effective diameter of the nanopore. With such a blockage, the fluidic solution resistance of the nanopore and the access resistance of both reservoirs increase above the resistance of the nanopore and access resistance of both reservoirs with no molecule present in the nanopore.

The partial blockage of the nanopore by a species object effects the nanopore solution resistance and the reservoir access resistances differently, as explained in detail below. As a result, the partial blockage of the nanopore by a translocating species causes a corresponding redistribution of electrical voltage occurs between the nanopore and the cis and trans reservoirs solutions, and the electrical potential at sites throughout the nanopore sensor accordingly adjusts. The local electrical potential at both the sites denoted as A and B in FIG. 2A thereby changes accordingly with this change in nanopore solution resistance and redistribution of voltage between the reservoir solutions and the nanopore. A measurement of electrical potential at either of these sites, or at another site of the nanopore sensor configuration, or a measurement of a difference in local potential between two or more sites, thereby provides an indication of the translocation of the molecule through the nanopore.

The local electrical potential at a selected nanopore sensor site and changes in this potential can be sensed by, e.g., changes in the conductance of the conducting channel in a transistor device. Transistor channel conductance therefore can be employed as a direct indication of the electrical potential local to the physical location of the transistor channel. Thus, the nanopore sensor arrangements of FIGS. 1A-1B correspond to a local electrical potential measurement at site A in the circuit 35 of FIG. 2A. The nanopore sensor arrangements of FIG. 1C-1D correspond to a local electrical potential measurement at site B in the circuit 35 of FIG. 2A. The nanopore sensor arrangement of FIG. 1E corresponds to a local electrical potential measurement at both sites A and B in the circuit 35 of FIG. 2A, and enables a determination of the difference between the potential at those two sites.

Figure 2B:
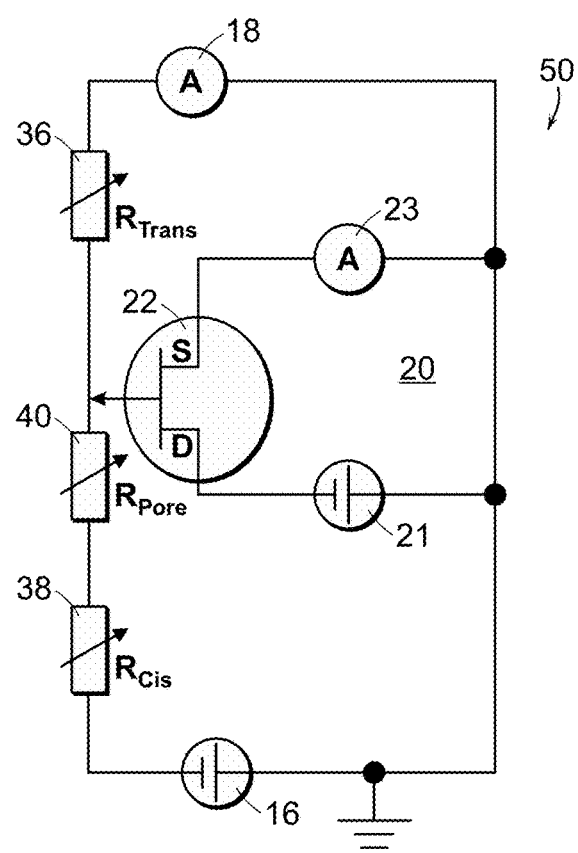
FIG. 2B is a circuit diagram for the nanopore sensor transistor implementation of FIG. 1B.

An electrical circuit equivalent of the example configuration of FIG. 1B is shown in FIG. 2B. Here is represented the access resistances of the cis and trans reservoirs, $R_{Cis}$, $R_{Trans}$, respectively, and the fluidic solution resistance, $R_{Pore}$, of the nanopore. The location of a device for measuring local potential, e.g., the channel of a transistor 22, is here positioned at the site A in FIG. 2A, providing a local electrical potential indication in the trans reservoir at the trans reservoir side of the nanopore. With this arrangement, as species objects such as molecules translocate through the nanopore, the output signal of the electrical potential measurement circuit can be monitored for changes in electrical potential, corresponding to changes in the state of the nanopore and the presence or absence of one or more objects in the nanopore.

This analysis can be applied to any nanopore sensor in which there is provided a local electrical potential measurement circuit and/or device. The analysis is not limited to the FET implementation described above, and is applicable to all of the implementations shown above, as well as others. All that is required is the provision of a device or circuit that makes a local electrical potential measurement as species objects translocate through the nanopore.

Figure 3A:
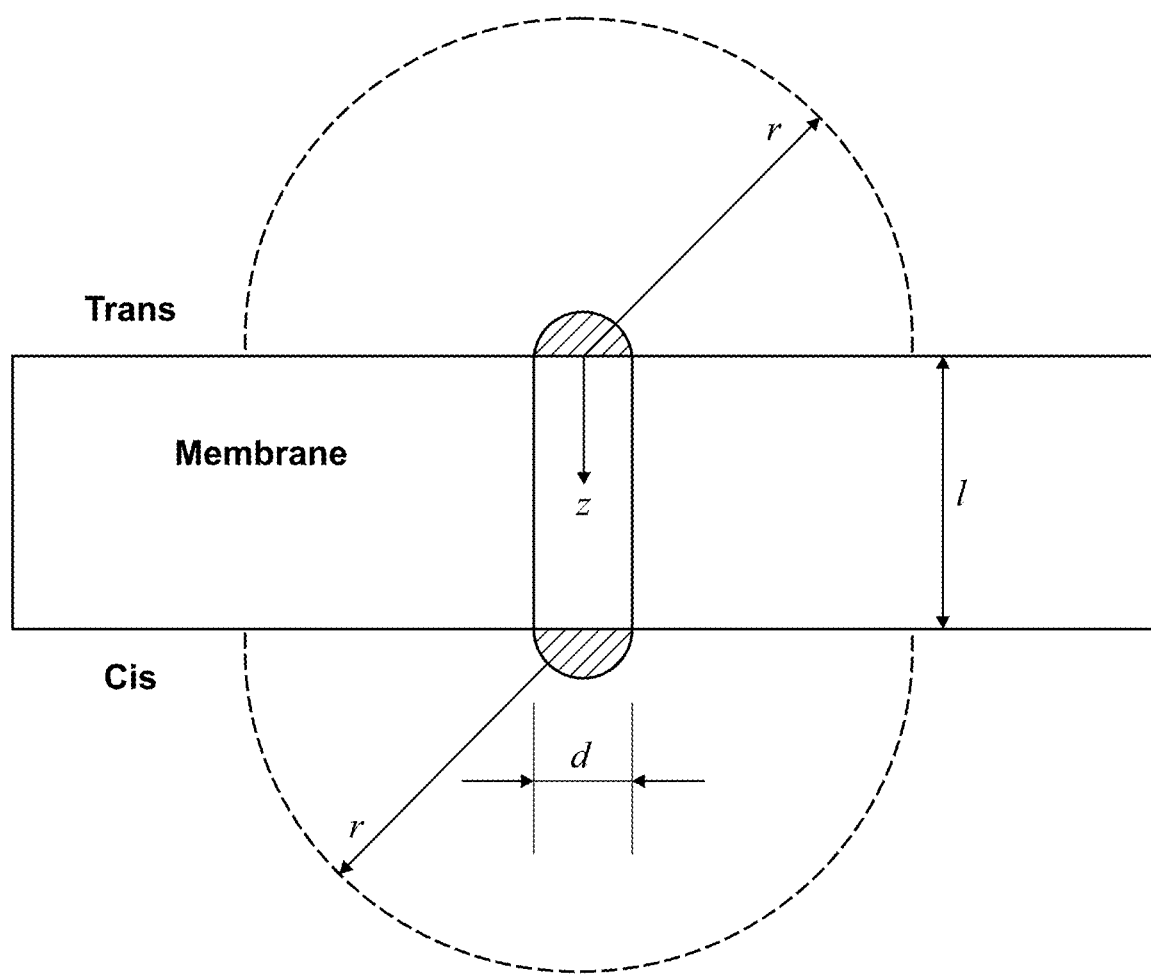
FIG. 3A is a schematic side view of the geometric features of a nanopore sensor configuration for measuring local electrical potential as-defined for quantitative analysis of the sensor.
Figure 3B:
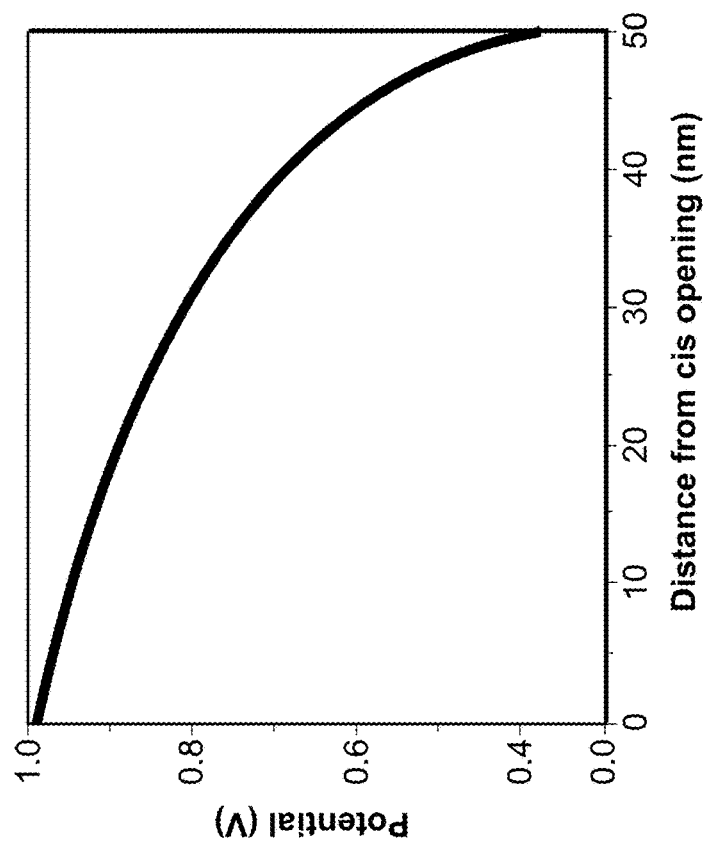
FIGS. 3B-3C are plots of the electrical potential in a nanopore of a nanopore sensor for measuring local electrical potential, here plotted as a function of distance from the nanopore into the cis reservoir, for a configuration in which the cis and trans reservoirs include fluidic solutions of equal ionic concentration and for a configuration in which the cis and trans reservoirs include fluidic solutions of unequal ionic concentration, respectively.
Figure 3C:
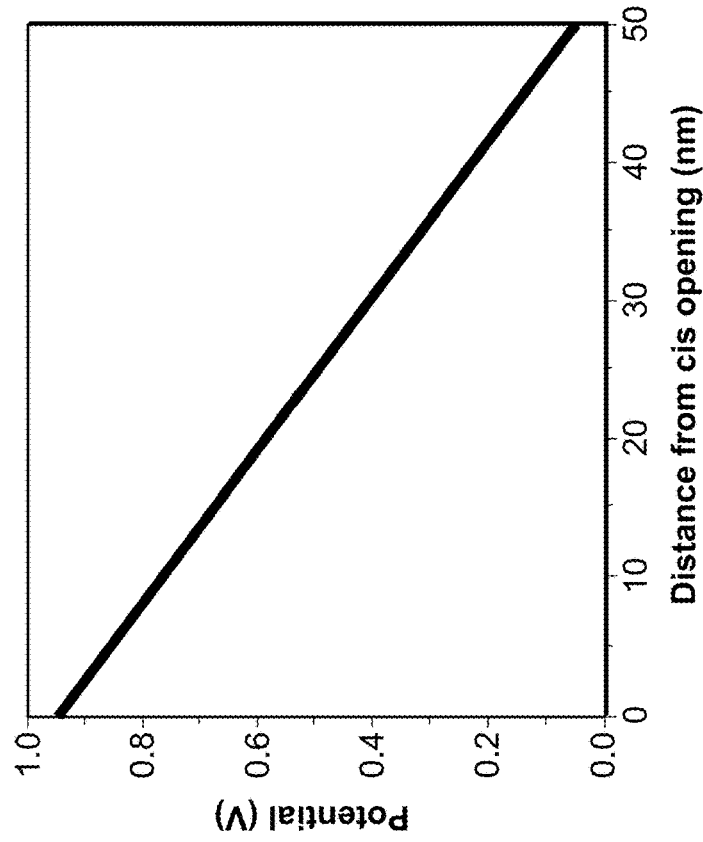
Figure 3E:
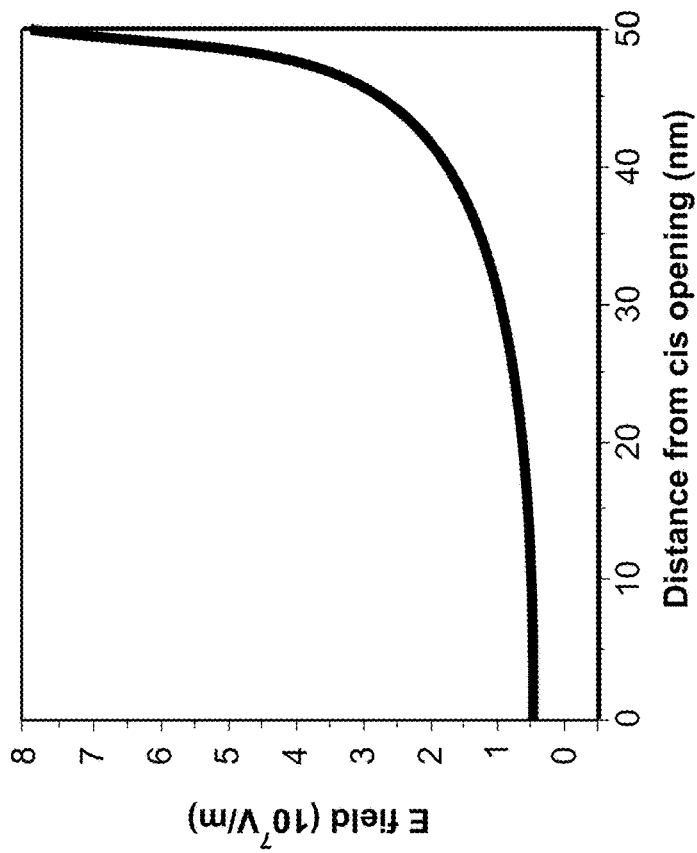
FIGS. 3D-3E are plots of the electrical field in a nanopore of a nanopore sensor for measuring local electrical potential, corresponding to the plots of electrical potential of FIGS. 3B-3C, respectively.

To further analyze the nanopore sensor system parameters, the nanopore sensor can be modeled as shown in the schematic representation of FIG. 3A. Several assumptions can be employed to enable an analytical calculation. First, the geometrical change of the membrane, nanopore, or other region of the nanopore sensor that is caused by the inclusion of a local potential sensing device or circuit can be ignored and the potential sensing device can be modeled as a point potential detector. The reservoirs are assumed to include electrically conductive ionic solutions. The two reservoir solutions are specified to be characterized by differing ionic concentrations. With this specification, the concentration distribution through the nanopore system is determined by the steady state diffusion that is driven by the cis/trans reservoir concentration difference. A further assumption can be made by approximating the buffer concentration distribution and electrical potential as being constant in small hemispheres on both sides of the nanopore. The nanopore sensor is assumed to be in steady state. Under these conditions, the diffusion equations of the nanopore sensor are given as:

$$\begin{cases} \dfrac{\partial C}{\partial t} = 0 & \left(\begin{array}{c}\text{For both chambers and inside}\\ \text{the nanopore}\end{array}\right) \\ r\dfrac{\partial^2 C(r)}{\partial r^2} + 2\dfrac{\partial C(r)}{\partial r} = 0 & \text{(For both chambers)} \\ \dfrac{\partial C(z)}{\partial z} = const & \text{(Inside the nanopore)} \end{cases} \quad (1)$$

Where C is concentration, t is time, r is location in a reservoir at a point measured from the nanopore, and z is distance through the nanopore length. If these diffusion equations are solved under the boundary conditions that in the cis reservoir far away from the nanopore, $C=C_{Cis}$, in the trans reservoir far away from the nanopore, $C=C_{Trans}$, the flux is the same in the nanopore and for both reservoirs, and the concentration is continuous at the nanopore opening in each reservoir, then the ionic concentration of the two reservoirs and the nanopore can be given as:

$$\begin{cases} C_C(r) = C_{Cis} - \dfrac{C_{Cis} - C_{Trans}}{4(2l+d)} \dfrac{d^2}{r} & (\textit{Cis chamber}) \\ C_T(r) = C_{Trans} - \dfrac{C_{Trans} - C_{Cis}}{4(2l+d)} \dfrac{d^2}{r} & (\textit{Trans chamber}) \\ C_P(z) = C_{Trans} + \dfrac{C_{Cis} - C_{Trans}}{2(2l+d)}(4z+d) & (\textit{Nanopore}) \end{cases} \quad (2)$$

Here l and d are thickness of membrane or other support structure and nanopore diameter, respectively. Because the ionic concentration distribution is therefore known and the solution conductivity is proportional to the concentration, then the conductivity of solution, σ, is given as:

$$\sigma = \Sigma \cdot C. \quad (3)$$

Here Σ is the molar conductivity of solution. Assuming the total current is I, then the electrical potential drop through the nanopore sensor, with a cis reservoir voltage, $V_C$, a trans reservoir voltage, $V_T$, and a nanopore voltage, $V_P$, can be given as:

$$\begin{cases} dV_C(r) = \dfrac{Idr}{2\pi \Sigma C_C(r) r^2} & (\textit{Cis chamber}) \\ dV_T(r) = \dfrac{-Idr}{2\pi \Sigma C_T(r) r^2} & (\textit{Trans chamber}) \\ dV_P(r) = \dfrac{4Idz}{\pi \Sigma C_P(z) d^2} & (\textit{Nanopore}) \end{cases} \quad (4)$$

If these three equations are solved with boundary conditions that far away from nanopore in the cis reservoir the electrical potential equals the voltage applied across the structure or membrane, i.e., a transmembrane voltage (TMV), to electrophoretically drive an object through the nanopore, and that far away from nanopore in the trans chamber, the potential is 0 V, then the voltages in the nanopore sensor, namely, the voltage in the cis reservoir, $V_C(r)$, the voltage in the trans reservoir, $V_T(r)$, and the voltage in the nanopore, $V_P(r)$, are given as:

$$\begin{cases} V_C(r) = V + \dfrac{2I(2l+d)}{\pi\Sigma(C_{Cis}-C_{Trans})d^2}\ln\left(1 - \dfrac{(C_{Cis}-C_{Trans})d^2}{4(2l+d)C_{Cis}r}\right) \\ V_T(r) = \dfrac{2I(2l+d)}{\pi\Sigma(C_{Cis}-C_{Trans})d^2}\ln\left(1 + \dfrac{(C_{Cis}-C_{Trans})d^2}{4(2l+d)C_{Trans}r}\right) \\ V_P(r) = \dfrac{2I(2l+d)}{\pi\Sigma(C_{Cis}-C_{Trans})d^2}\ln\left(\dfrac{(4l+d)C_{Trans}+dC_{Cis}+4(C_{Cis}-C_{Trans})z}{2(2l+d)C_{Trans}}\right) \end{cases} \quad (5)$$

Because the electrical potential is continuous at both nanopore openings into the reservoirs and because the total voltage applied is V, Expression (5) can be further simplified to:

$$\begin{cases} V_C(r) = V + \dfrac{V}{\ln(C_{Cis}/C_{Trans})}\ln\left(1 - \dfrac{d^2(1-C_{Trans}/C_{Cis})}{4(2l+d)r}\right) \\ V_T(r) = \dfrac{V}{\ln(C_{Cis}/C_{Trans})}\ln\left(1 + \dfrac{d^2(C_{Cis}/C_{Trans}-1)}{4(2l+d)r}\right) \\ V_P(r) = \dfrac{V}{\ln(C_{Cis}/C_{Trans})}\ln\left(\dfrac{4l+d+dC_{Cis}/C_{Trans}+4(C_{Cis}/C_{Trans}-1)z}{2(2l+d)}\right) \end{cases} \quad (6)$$

With this expression, the electric field, $E_P(r)$ inside nanopore can be given as:

$$E_P(r) = \dfrac{dV_P(r)}{dz} = \quad (7)$$

$$\dfrac{4V(C_{Cis}/C_{Trans}-1)}{\ln(C_{Cis}/C_{Trans})} \dfrac{1}{4l+d+dC_{Cis}/C_{Trans}+4(C_{Cis}/C_{Trans}-1)z}.$$

With this expression, the electrical potential change at the trans reservoir side of the nanopore can be estimated by the electrical potential change due to a reduction in the nanopore area, A, by the presence of a species object, such as a molecule, in the nanopore, as:

$$\delta V_T|_{d/2} = \dfrac{\partial V_T}{\partial A}\bigg|_{d/2} \delta A = \dfrac{2\delta A V}{\pi\ln(C_{Cis}/C_{Trans})} \dfrac{(4l+d)(C_{Cis}/C_{Trans}-1)}{(2l+d)(d^2(C_{Cis}/C_{Trans}-1)+4(2l+d)r)}\bigg|_{d/2} = \quad (8)$$

$$\dfrac{2\delta A V}{\pi\ln(C_{Cis}/C_{Trans})} \dfrac{(4l+d)(C_{Cis}/C_{Trans}-1)}{(2l+d)(d^2(C_{Cis}/C_{Trans}+1)+4ld)}$$

Here δA is the cross-sectional area of the molecule.

The resistances of the nanopore sensor, namely, $R_{Cis}$, $R_{Trans}$, and $R_{Pore}$, can be computed based on the above expressions for voltage drop across the reservoirs and the nanopore as:

$$\begin{cases} R_{Cis} = \dfrac{-2(2l+d)}{\pi\Sigma(C_{Cis}-C_{Trans})d^2}\ln\left(1-\dfrac{(C_{Cis}-C_{Trans})d}{2(2l+d)C_{Cis}}\right) \\ R_{Trans} = \dfrac{2(2l+d)}{\pi\Sigma(C_{Cis}-C_{Trans})d^2}\ln\left(1+\dfrac{(C_{Cis}-C_{Trans})d}{2(2l+d)C_{Trans}}\right) \\ R_{Pore} = \dfrac{2(2l+d)}{\pi\Sigma(C_{Cis}-C_{Trans})d^2}\ln\left(\dfrac{(4l+d)C_{Cis}+dC_{Trans}}{(4l+d)C_{Trans}+dC_{Cis}}\right) \end{cases} \quad (9)$$

So, the total resistance and ionic current of the nanopore sensor are given as:

$$\begin{cases} R = R_{Cis}+R_{Trans}+R_{Pore} = \dfrac{2(2l+d)}{\pi\Sigma(C_{Cis}-C_{Trans})d^2}\ln\left(\dfrac{C_{Cis}}{C_{Trans}}\right) \\ I = V/R = \dfrac{\pi\Sigma(C_{Cis}-C_{Trans})d^2 V}{2(2l+d)\ln(C_{Cis}/C_{Trans})} \end{cases} \quad (10)$$

With these expressions, it is demonstrated that the electrical characteristics of the nanopore sensor, and in particular the distribution of electrical potential in the sensor, depends directly on the ionic concentration of the fluidic solutions in the cis and trans reservoirs. Specifically, the ratio of the reservoir solution concentrations directly impacts the magnitude of the change in local potential due to species translocation through the nanopore.

FIGS. 3B-3E are plots of electrical potential and electric field in the nanopore, demonstrating these conditions. Given a cis/trans buffer solution concentration ratio=1:1, a 50 nm-thick nitride membrane, a 10 nm diameter nanopore in the membrane, and a 1 V transmembrane voltage, i.e., 1 V applied between the solutions in the two reservoirs, then the electrical potential in the nanopore as a function of distance from the nanopore opening at the cis reservoir is plotted in FIG. 3B, based on Expression (6) above. That same potential is plotted in FIG. 3C for a condition in which the cis/trans buffer solution concentration ratio is instead 100:1. Note the increase in electrical potential at a given nanopore location for the unbalanced buffer solution ratio at points closer to the lower-concentration reservoir.

Figure 3D:
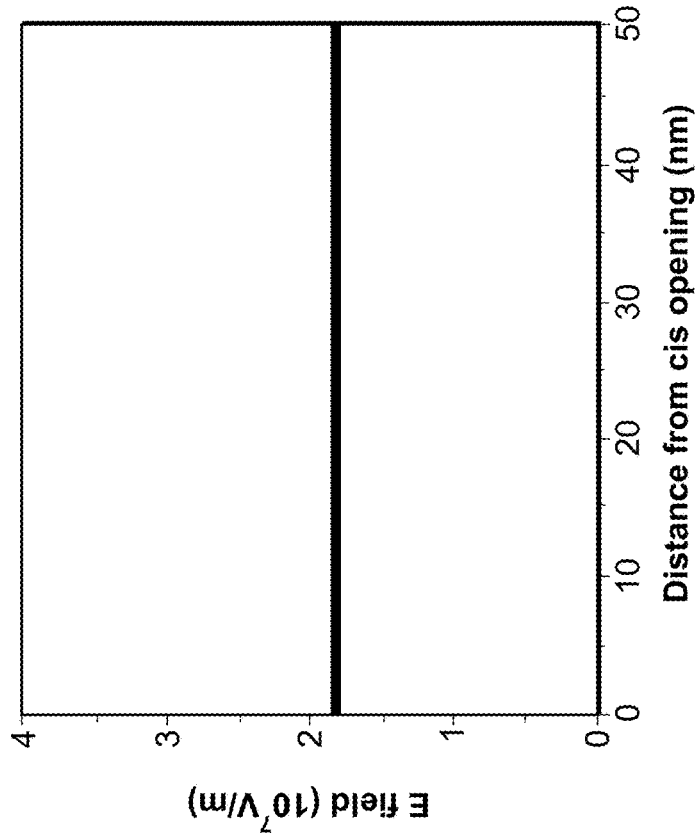

FIG. 3D is a plot of the electric field in the nanopore under the conditions given above, here for a balanced buffer solution ratio, based on Expression (7) above. That same electric field profile is plotted in FIG. 3E for a condition in which the cis/trans buffer solution concentration ratio is instead 100:1. Note the increase in electrical potential at a given nanopore location for the unbalanced buffer solution ratio, and that the electric field is dramatically stronger at points closer to the low concentration, higher resistance, reservoir.

With this finding, it is discovered that with a condition in which the reservoir solutions are both provided as electrically-conductive ionic solutions of the same ionic concentration, the ratio of the access resistance of the cis reservoir, $R_{Cis}$, the access resistance of the trans reservoir, $R_{Trans}$, and the solution resistance of the nanopore, $R_{Pore}$, are all fixed and the nanopore resistance is much larger than the reservoir access resistances. But under non-balanced ion concentration conditions, the reservoir having a lower ionic concentration has a larger access resistance, that can be on the order of the nanopore resistance, while the higher-ionic concentration reservoir resistance becomes comparably negligible.

Based on a recognition of this correspondence, it is herein discovered that to maximize a local potential measurement in the nanopore sensor, it is preferred that the ionic reservoir solutions be provided with differing ion concentrations. With this configuration of unbalanced ionic concentration, the local potential measurement is preferably made at a site in the reservoir which includes the lower ionic concentration. It is further preferred that the buffer concentration of the lower-ion concentration solution be selected to render the access resistance of that reservoir of the same order of magnitude as the nanopore resistance and much larger than the resistance of the high-ion concentration solution, e.g., at least an order of magnitude greater than that of the high-ion concentration solution, so that, for example, if the local potential measurement is being made in the trans reservoir:

$$R_T, R_P \gg R_C \quad (11)$$

Based on this discovery then, for a given nanopore diameter, which sets the nanopore resistance, $R_P$, it is preferred to decrease the ionic solution buffer concentration of the reservoir designated for local potential measurement to a level at which the access resistance of that reservoir is of the same order of magnitude as the nanopore resistance. This reservoir access resistance should not dominate the nanopore sensor resistance, but should be on the order of the nanopore resistance.

Figure 4A:
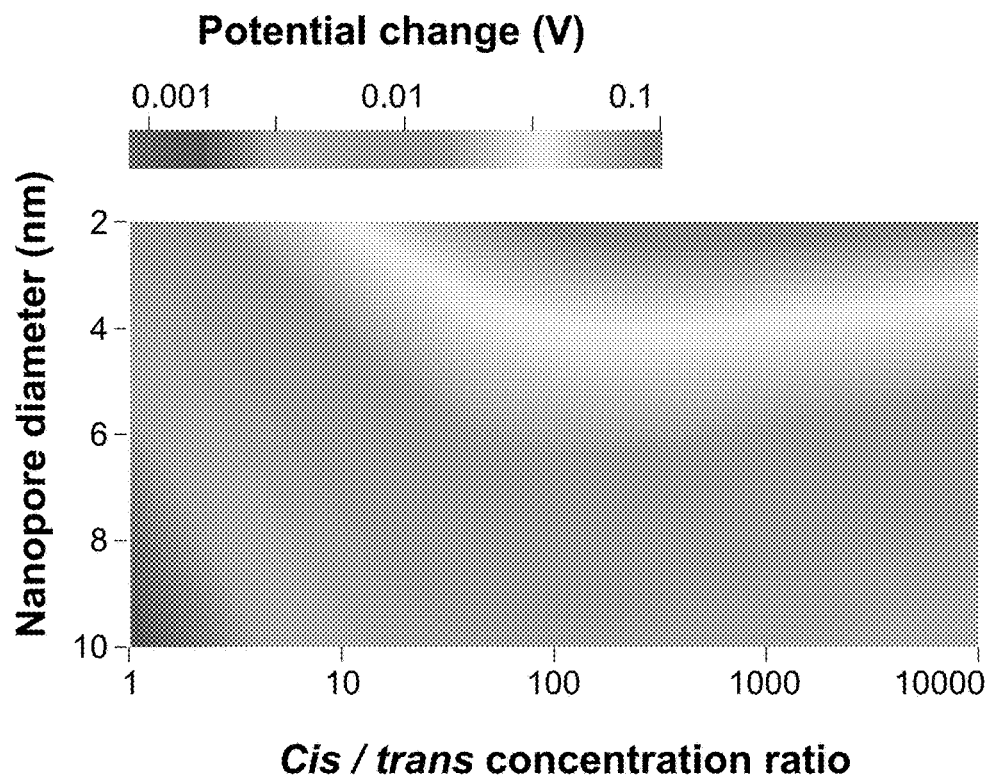
FIG. 4A is a plot of the change in potential in a nanopore for a 50 nm-thick nanopore membrane and a configuration of a 1 V transmembrane voltage (TMV) for electrophoretic species translocation as a dsDNA molecule translocates through the nanopore, as a function of the $C_{Cis}/C_{Trans}$ ionic concentration ratio for various nanopore diameters below 10 nm where the nanopore is configured for local electrical potential measurement.
Figure 4B:
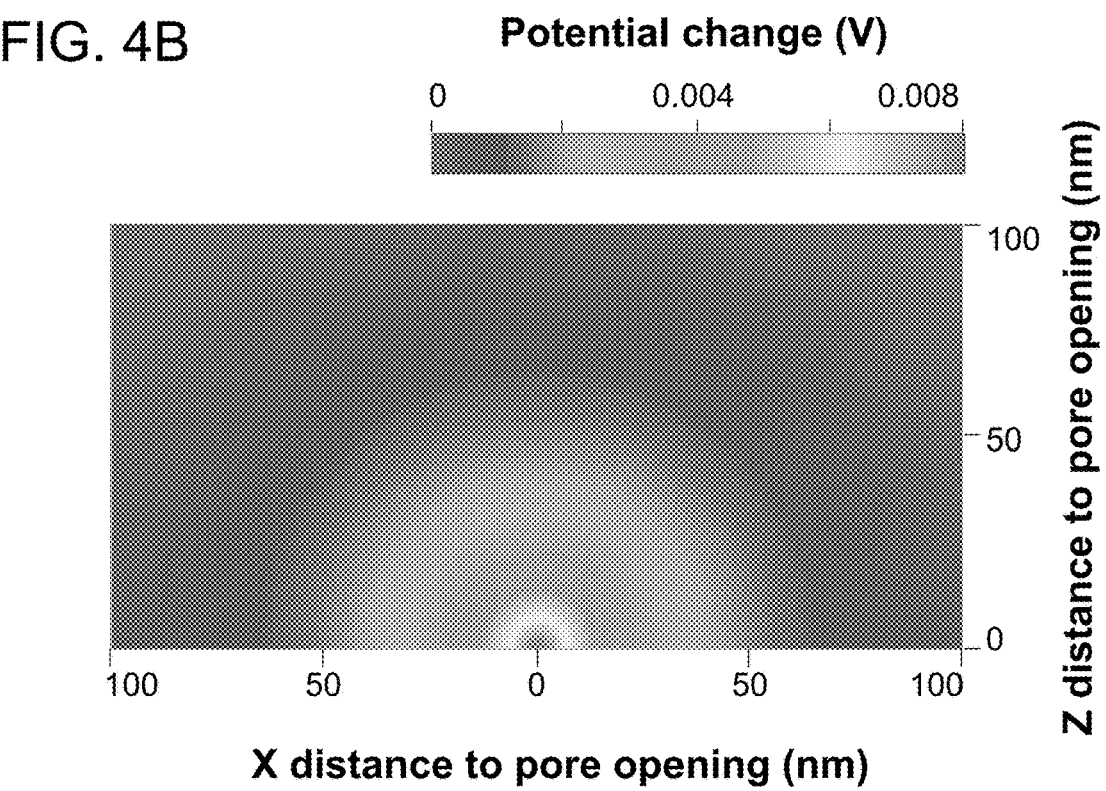
FIG. 4B is a plot of the change in potential in the trans reservoir for a 10 nm-diameter nanopore at 1 V TMV for the conditions of the plot of FIG. 4A.

This condition can be quantitatively determined directly by electrically modeling the nanopore sensor components in the manner described above. Based on Expression (8) above, there can be determined the ratio of solution concentrations that maximize the potential change during nanopore translocation of a selected object for given nanopore sensor parameters. For example, FIG. 4A is a plot of Expression (8) for a 50 nm-thick nanopore membrane and a configuration of a 1 V TMV for electrophoretic species translocation as a dsDNA molecule translocates through the nanopore. The potential change is shown as a function of the $C_{Cis}/C_{Trans}$ ionic concentration ratio for various nanopore diameters below 10 nm. From this plot, it is found that the local potential change in the trans reservoir is maximized for a ~100:1 $C_{Cis}/C_{Trans}$ chamber buffer concentration ratio for any nanopore diameter modeled here. FIG. 4B is a plot of the corresponding calculated potential change distribution in the trans reservoir for a 10 nm-diameter nanopore at 1 V TMV for the selected 100:1 $C_{Cis}/C_{Trans}$ solution concentration ratio.

This demonstrates that based on the discovery herein, for a given reservoir site that is selected for making electrical potential measurements, the ratio of ionic fluid buffer concentration in the two reservoirs is to be selected with the lower buffer concentration solution in the measurement reservoir, to maximize the amplitude of the electrical potential changes at that selected measurement site. The distribution of this resulting potential change is highly localized within several tens of nanometers of the nanopore, as shown in FIG. 4B. For the example 100:1 $C_{Cis}/C_{Trans}$ solution concentration ratio and nanopore parameters given just above, it can be determined, e.g., based on Expression (9) above, that the access solution resistance of the trans reservoir and the solution resistance of the nanopore are indeed within the same order of magnitude.

With this arrangement of reservoir fluidic solution buffer concentrations and potential measurement configuration, it is noted that the local potential sensing technique of produces a local potential measurement signal that depends on the trans-membrane voltage (TMV) and the ionic current signal. Other sensor based nanopore technologies generally rely on a direct interaction between a translocating species and the nanopore sensor through, e.g., electrical coupling or quantum mechanical tunnelling. For these techniques, the nanopore output signal is typically not directly related to the TMV or ionic current and should not change significantly when the TMV is changed. In contrast, in the local potential measurement system herein, the nanopore sensor signal is proportional to the TMV and can be regarded as a linear amplification of the ionic current signal. As a result, both the local potential measurement signal and the ionic current signal amplitudes depend on the TMV linearly, but the ratio between them is a constant for a given nanopore geometry and reservoir solution concentrations, as evidenced by the expressions given above.

An advantage of the local potential measurement method is the characteristically high-bandwidth capability of the measurement with low noise. Low signal bandwidth is one of the issues that limits direct nanopore sensing by the conventional ionic current blockage measurement technique, due to the difficulties of high bandwidth amplification of very small measured electrical current signals. This can be particularly true for a small nanopore when employed for DNA sensing. In the local potential sensing method, a large local electrical potential signal is measured instead of a small current signal, so the signal bandwidth is not limited by the capabilities of a current amplifier. As a result, high-bandwidth signal processing electronics can be integrated on a solid state nanopore sensing structure.

Further, except for intrinsic shot noise and Johnson noise, the majority of noise contributions to an ionic current blockage measurement technique are introduced through the capacitive coupling cross a nanopore membrane and this capacitive coupling component of noise can be overwhelming at certain stages of nanopore operation. Conventionally, a very small membrane area exposure to a reservoir solution is required in an effort to minimize noise. In the local potential measurement method herein, because the local potential signal decays within a few tens of nanometers around the nanopore for reasonable reservoir concentration ratios, the local potential measurement signal is only affected by capacitive coupling between reservoir solutions within this local volume. Therefore, the majority of capacitive coupling noise is automatically rejected in the local electrical potential measurement sensing method.

Figure 4C:
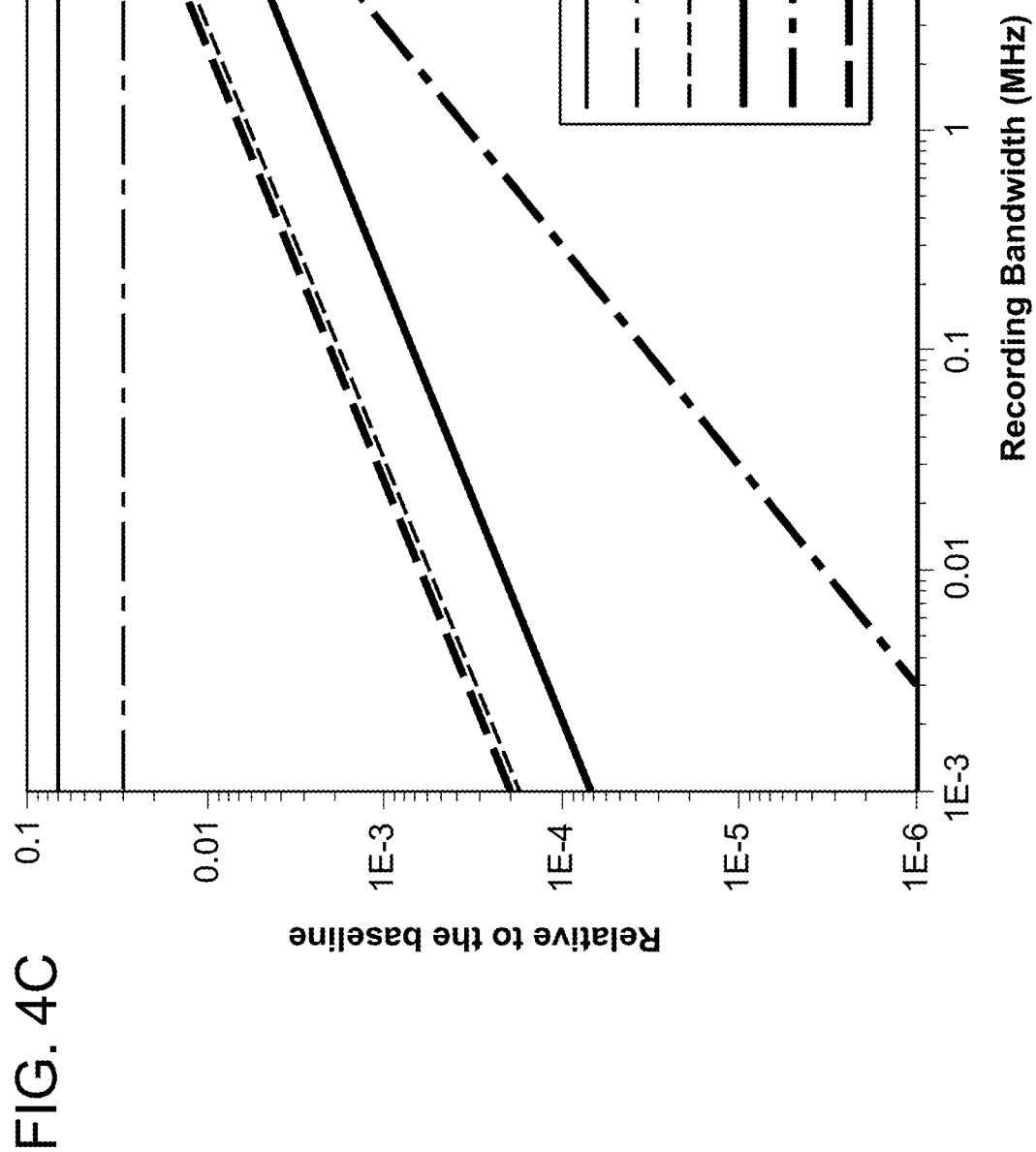
FIG. 4C is a plot of noise sources and signal as a function of recording bandwidth for a nanopore sensor configured for local electrical potential measurement.
Figure 4D:
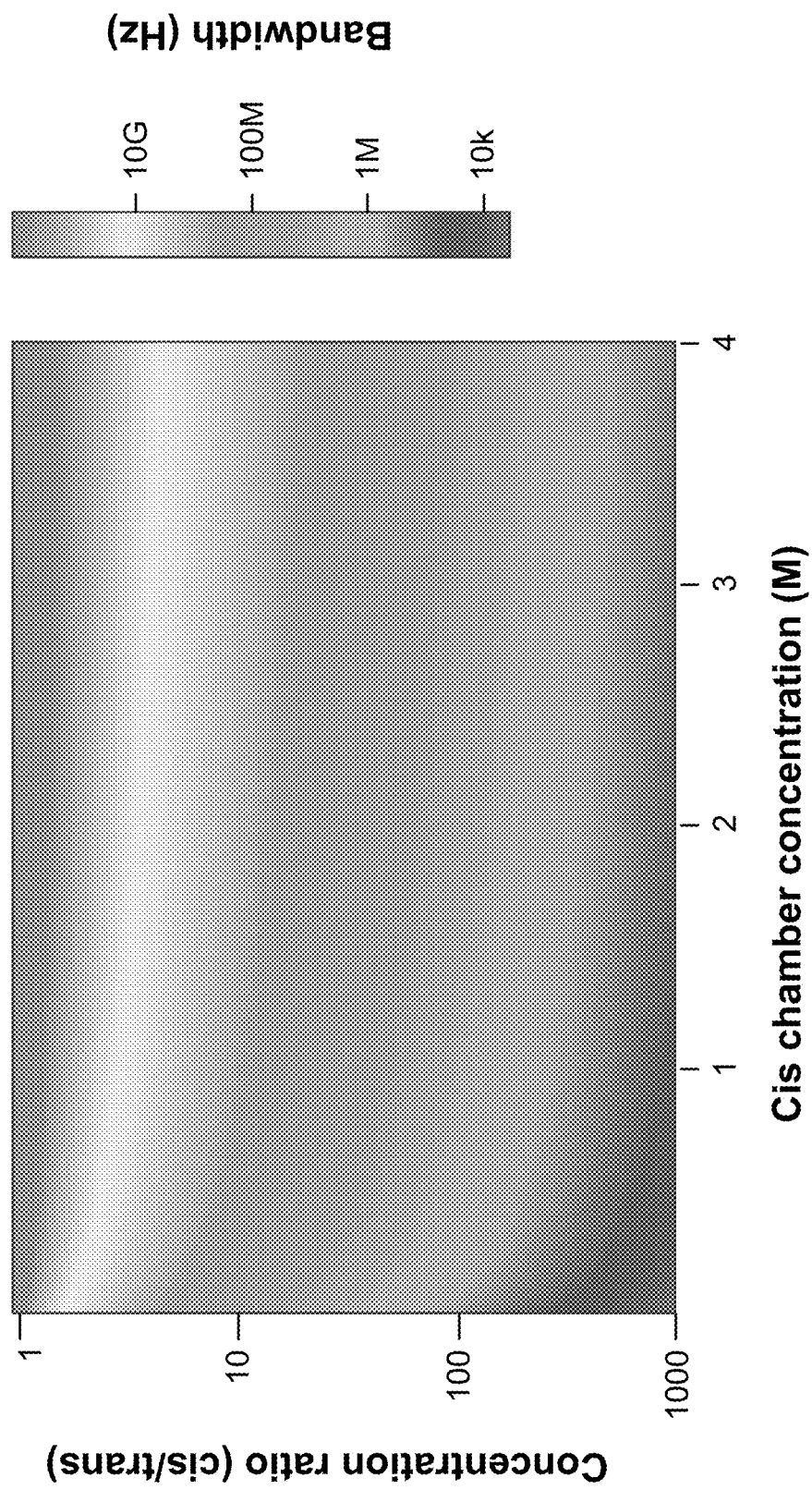
FIG. 4D is a plot of the bandwidth of a nanopore sensor configured for local electrical potential measurement as a function of cis chamber solution concentration for a range of reservoir solution concentration ratios.

Referring to FIGS. 4C-4D, the reservoir buffer solution concentration ratio can be selected to optimize the signal bandwidth of the nanopore sensor. Given that the local potential measurement is to be made in the trans side of the nanopore, then the cis reservoir solution concentration is set as high as reasonable, e.g., about 4 M, about a saturated solution, to minimize the nanopore solution resistance. Then, the signal noise as a function of bandwidth is analyzed, e.g., based on the plot of FIG. 4C. Here are plotted the various contributions to noise as well as the signal expected for a fluidic nanopore operation. The plot labelled "free space" refers to a computation based on free-space molecular size. The plot labelled "Bayley" refers to computation based on molecular size from previous work by Bayley et al, in J. Clarke et al., "Continuous Base Identification for Single-Molecule Nanopore DNA Sequencing," *Nature Nanotechnology*, N. 4, pp. 265-270, 2009. The two signal lines are the minimum signal difference that is attained between the four DNA bases, which minimum signal exists between the A and the T bases. Here the nanopore is given as a 1 nm-diameter nanopore in a graphene membrane, with a 4 M cis reservoir solution concentration, a buffer concentration ratio between the reservoirs of 50:1, and a voltage noise density of about $10^{-9}$ V/√Hz. The dielectric loss factor for graphene is unknown, so 1 was used for convenience. Finding the cross point of the signal and total noise in the plot sets the 1:1 signal-to-noise ratio (S/N). This is the highest possible signal bandwidth. For example, for the fluidic nanopore operation, the 1:1 S/N ratio is at a bandwidth of about 100 MHz. A bandwidth greater than about 50 MHz can be preferred as well as the 100 MHz bandwidth.

Referring to the plot of FIG. 4D, the 100 MHz bandwidth corresponds to reservoir solution concentration ratio of about 50:1, where the local potential measurement is to be made in the low-concentration reservoir side of the nanopore. For the nanopore sensor parameters used in this example, any reservoir concentration ratio higher than about 50:1 will decrease the bandwidth. Any concentration ratio lower than about 50:1 will decrease the signal-to-noise ratio. Therefore, it is discovered herein that the bandwidth can be optimized and there exists an optimization point of reservoir concentration ratio. The reservoir solution concentration ratio is therefore selected based on a trade-off between the characteristic noise of the nanopore sensor and the desired operational bandwidth of the nanopore sensor. It is to be recognized therefore that to minimize noise, the reservoir solution concentration ratio can be increased, but that the bandwidth may be correspondingly reduced. Alternatively, electronic signal processing, such as low-pass filtering, or other processing of the signal, can be employed.

It is further to be recognized that in general, a smaller nanopore produces a larger signal for a given species object to translocate through the nanopore. For applications such as sensing a particular molecule, such as DNA, however, the nanopore extent is preferably sized based on the molecule, and the tuning of the reservoir concentration ratio is made accordingly.

Figure 4E:
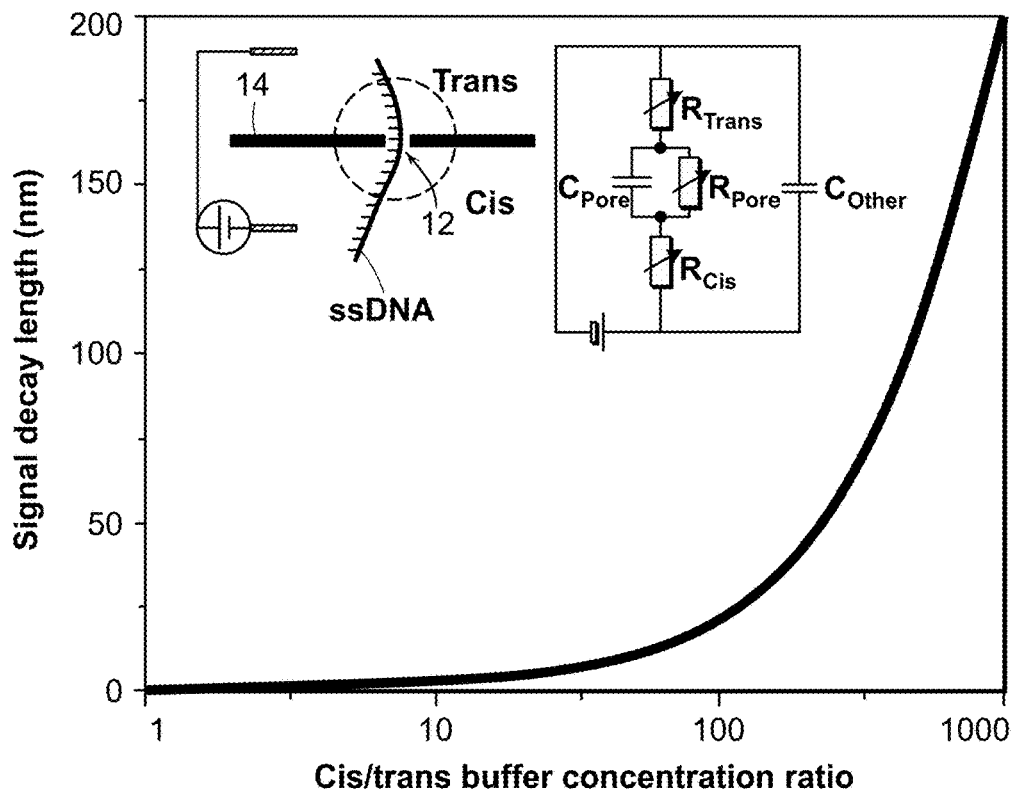
FIG. 4E is a plot of signal decal length from the nanopore site in a nanopore configured for local electrical potential measurement as a function of cis and trans reservoir solution concentration ratio.

The reservoir buffer solution concentration ratio can also be selected to produce a signal decay length, measured from the site of the nanopore, that accommodates a selected local potential measurement device. It is recognized that the decay length of the signal should be sufficiently large to accommodate the arrangement of a potential measurement device within the decay length. FIG. 4E is a plot of signal decay length for a range of buffer concentration ratios, given that the local potential measurement is to be made on the trans reservoir side of the nanopore. The plot is based on the circuit model shown inset in the plot.

Based on this analysis, it is shown that at concentration ratios greater than about 20 or 30, there is produced a sufficient decay length to accommodate a device that can measure the local electrical potential within the decay length. At concentration ratios greater than about 50:1, ample decay length is provided for making a potential measurement within the decay length. A signal decay length greater than about 5 nm can be preferred, as well as a signal decay length of, e.g., about 10 nm and about 20 nm.

Turning to implementation of a local potential measurement device, as explained above, a local electrical potential measurement can be made in the nanopore sensor with any suitable device or circuit that accommodates the nanopore implementation. For many applications, a nanowire-based FET device can be a well-suited device, but such is not required herein. The SET, QPC, lipid bilayer, or other device and nanopore implementation, whether biological or solid state, can be employed. Any circuit or device that enables a local potential measurement can be employed.

Figure 5:
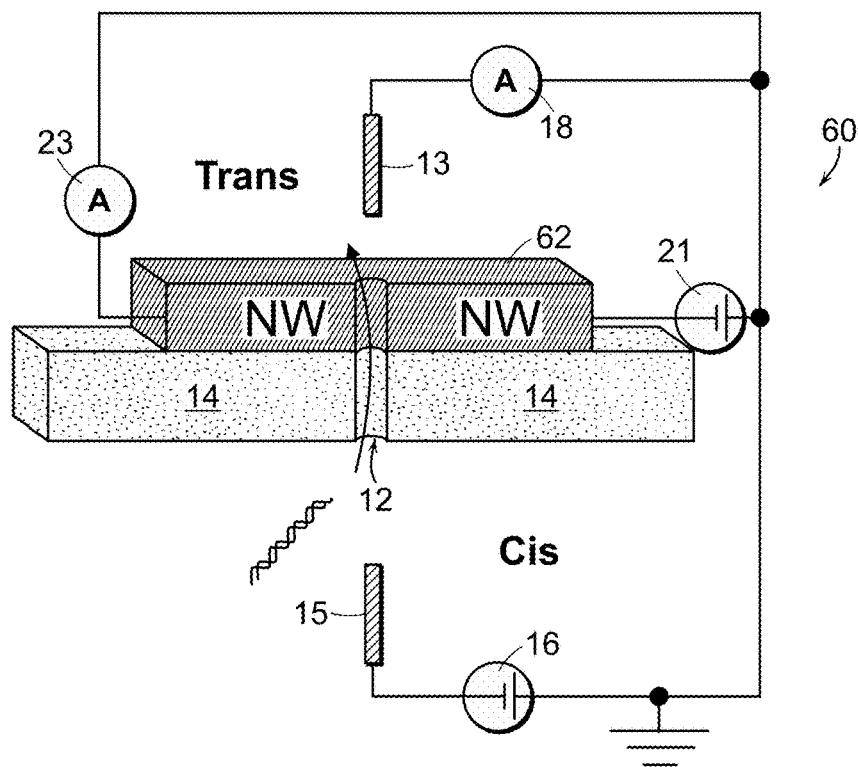
FIG. 5 is a schematic view of a nanopore sensor configured for local electrical potential measurement with a nanowire FET disposed on a membrane.

In one example, a nanowire FET can be configured at the site of the nanopore as shown in FIG. 5. In this nanowire implementation 60, there is provided a nanowire 62 on the support structure or membrane 14 in which is disposed the nanopore 12. The nanowire can be formed of any suitable electrically conducting or semiconducting material, including fullerene structures and semiconducting wires. The term "nanowire" as used herein refers to an electrical conduction channel that is characterized by a width that is compatible with the signal decay length measured from the nanopore site as described above. The channel width is preferably on the same order of magnitude as the decay length and can be larger. The nanowire can be made from any semiconductor material that is stable in the selected reservoir solution.

Figure 6:
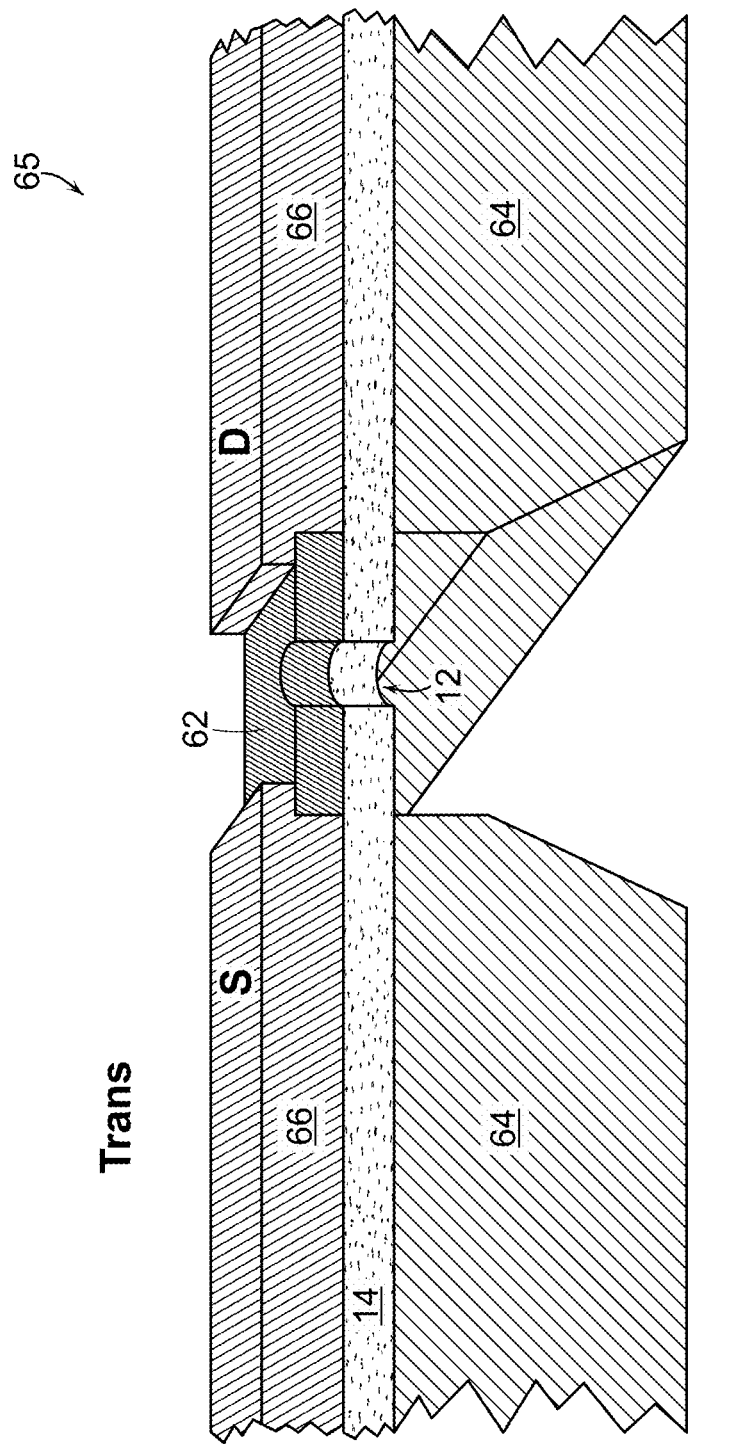
FIG. 6 is a perspective view of one example implementation of the nanopore sensor configuration of FIG. 5.

FIG. 6 is a perspective view of an example implementation 65 of the nanopore sensor of FIG. 5. Here is shown the nanowire 62 provided on a membrane 14 that is self-supported and that is disposed on a support structure 64 such as a substrate. The nanowire is provided on the membrane with a nanopore extending through the thickness of the nanowire and the membrane. As shown in FIGS. 5 and 6, the nanopore 12 does not extend across the width of the nanowire. There is a region 66 of the nanowire that is unbroken along the extent of the nanopore so that electrical conduction is continuous along the length of the nanowire. A metallization region or other electrically conducting region is provided at each end of the nanowire to form source (S) and drain (D) regions. With this configuration, the nanopore sensor can be configured with cis and trans reservoirs as shown for detecting translocation of species from one reservoir through the nanopore to the other reservoir.

Figure 8B:
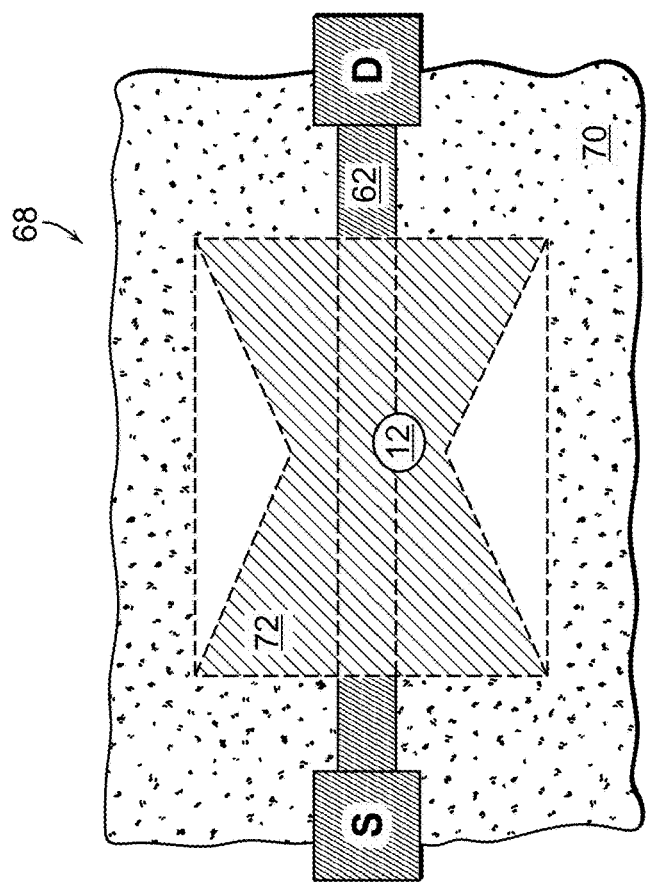
FIGS. 8A-8B are a schematic view of a nanopore sensor configured for local electrical potential measurement with a graphene layer disposed on a nanowire FET, and a plan view of an example implementation of this nanopore sensor, respectively.
Figure 8A:
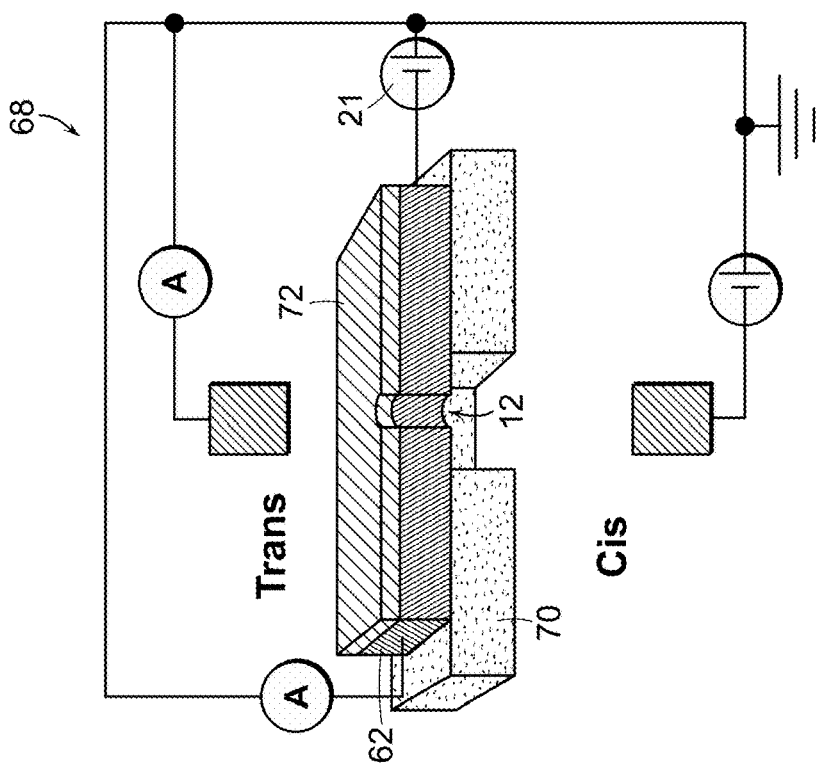

Referring also to FIGS. 7A-7B, the membrane and nanowire configuration can be implemented in a variety of alternative arrangements, and the membrane is not required for applications in which a nanowire material is self-supporting and can itself function as a support structure in which the nanopore is disposed. For example, as shown in FIGS. 7A-B, in a graphene-based nanopore sensor 68, there can be provided a membrane 70, which in turn supports a graphene membrane 72. The graphene membrane 72 is self-supported across an aperture in the membrane 70. The graphene membrane in turn supports a nanowire 62, with a nanopore 12 extending through the thickness of the nanowire and the graphene, and the nanowire remaining continuous along some point of the nanowire. As shown in FIGS. 8A-8B, this arrangement can be altered, with the nanowire 62 instead disposed under the graphene layer 72, on a membrane 70.

Figure 9B:
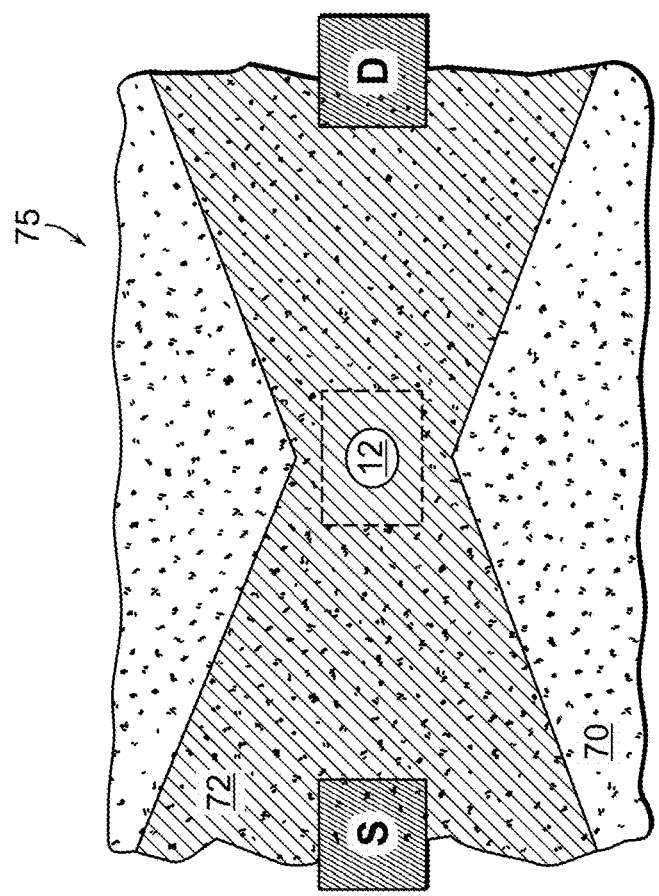
FIGS. 9A-9B are a schematic view of a nanopore sensor configured for local electrical potential measurement with a graphene membrane, and a plan view of an example implementation of this nanopore sensor, respectively.
Figure 9A:
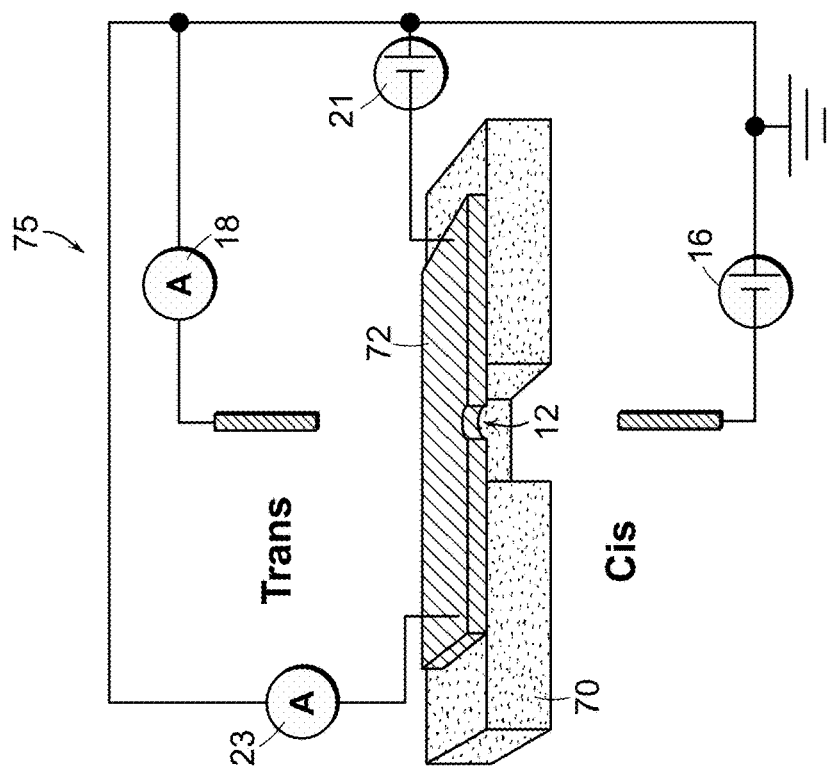

In an alternative graphene-based nanopore sensor 75, as shown in FIGS. 9A-9B, there can be configured a support structure, such as a membrane 70, on which is disposed a graphene layer 72 that functions to provide a structure in which a nanopore 12 is configured and that itself functions to provide a nanowire. The graphene can be provided in any suitable geometry that provides the requisite nanowire at the site of the nanopore 12. In this configuration, the graphene layer 72, due to its thickness and conductivity, senses the local electrical potential on both sides of the nanopore, i.e., the conductance of the graphene layer changes as a function of the local potential in both the trans and cis reservoirs. The nanopore sensor signal of a local potential measurement is therefore for this graphene-based nanopore sensor an indication of the difference between the cis and trans reservoir potentials.

As demonstrated by these example arrangements, the membrane, nanowire, and support structure can be configured with any in a wide range of materials combinations and thicknesses. For many applications, it can be preferred that the structure in which the nanopore is disposed be as thin as possible, and preferably no thicker than the extent of a species object, or object region to be detected. Example membrane materials include nitrides, oxides, graphene, plastics, or other suitable material, which can be electrically insulating or electrically conducting.

Figure 10B:
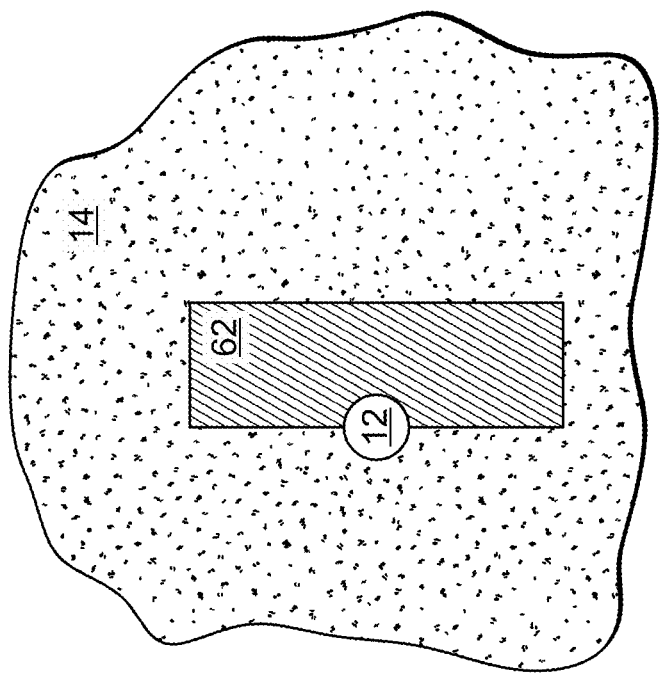
FIGS. 10A-10D are schematic plan views of example locations of a nanopore with respect to a nanowire in a nanopore sensor configured for local electrical potential measurement.
Figure 10A:
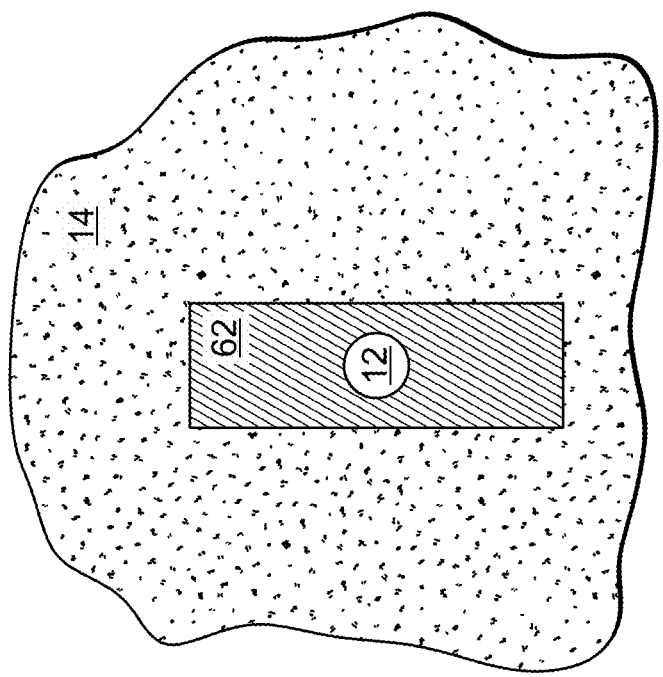
Figure 10D:
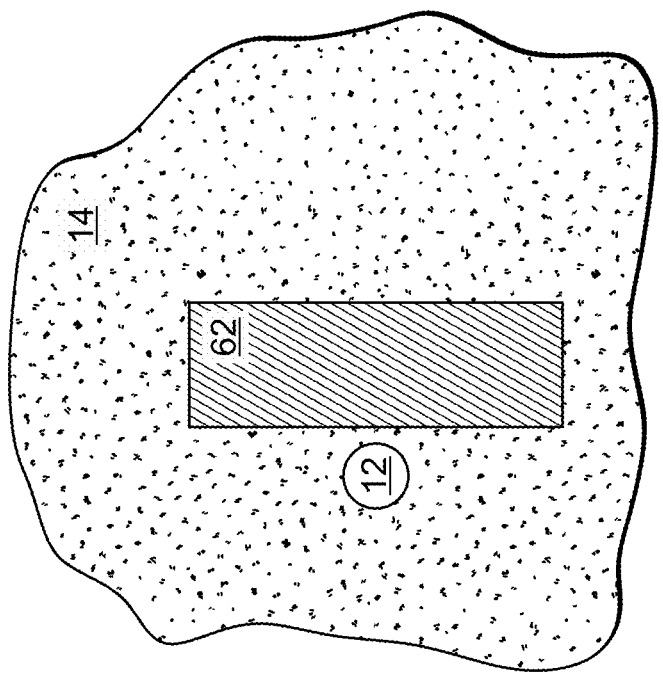
Figure 10C:
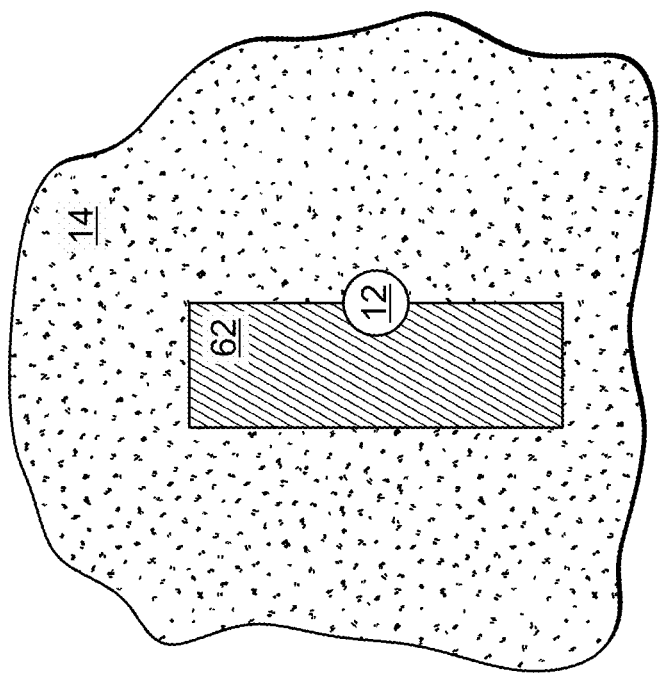

As shown in FIGS. 10A-10D, for a nanowire implementation, the nanopore is provided at the location of a nanowire 62 such that an unbroken, continuous path for electrical conduction is provided through the nanowire. The nanopore can be provided at a central region of the nanowire, as depicted in FIG. 10A, can be provided at an edge of the nanowire, as depicted in FIGS. 10B-10C, or can be provided at a site near to or adjacent to the nanowire, as depicted in FIG. 10D. In all cases, a continuous path for electrical conduction is provided through the nanowire.

In the nanopore arrangements of FIGS. 10A-10C, it is found that the sensitivity of the nanopore region is also significantly enhanced compared to the sensitivity of the same region prior to nanopore drilling. This sensitivity localization can be understood by a model accounting for the reduction of the cross-sectional area of the nanowire as a conduction channel, assuming all other material properties, such as doping level and mobility remain unchanged. The reduced cross-sectional area of the nanowire increases the resistance of the nanopore region and therefore alleviates series resistance and signal attenuation from other portions of the nanowire. Quantitatively, this sensitivity enhancement at the nanopore region can be obtained from the following equation for a rectangular-shaped nanopore as an example:

$$\Delta = \left(\frac{\rho_0 L}{\rho(L-L_0)+\rho_0 L_0}\right)^2. \tag{12}$$

Here, $\Delta$ is the sensitivity enhancement defined as the sensitivity of the device with a nanopore divided by the sensitivity without the nanopore, and $\rho_0$ and $\rho$ are the linear resistivities of the nanowire conduction channel with and without the nanopore, respectively. L is the total channel length and $L_0$ is the channel length of the nanopore region, which for this square example is equal to the side length of the nanopore along the nanowire axial direction. For other portions of nanowire, because all parameters remain the same but the total channel resistance is increased slightly due to the nanopore, the sensitivity should decrease slightly after nanopore drilling. The combination of increased sensitivity at the nanopore region and decreased sensitivity of all other nanowire portions makes the sensitivity of a nanopore sensor enhanced, self-aligned and localized at the nanopore.

In fabrication of the nanopore sensor, first considering a nanowire-based solid state nanopore sensor, a short-channel nanowire can be preferred, and for many applications, a silicon nanowire (SiNW) can be preferred because the SiNW has been demonstrated as an excellent electrical potential and charge sensor for sub-cellular and single-virus level signaling with remarkable stability in solution. To minimize signal attenuation from channel series resistance, the SiNW channel can be reduced, if desired, to less than about 200 nm by nickel solid-state diffusion. SiNWs can be fabricated by, e.g., chemical vapor deposition, or other suitable process, and disposed on a selected membrane, such as a nitride membrane, by solution. For many applications, a commercially-available nitride membrane chip can be suitably employed. Electron beam lithography or optical lithography can be employed for producing source and drain electrodes at ends of the nanowire. All electrodes and electrical contacts are to be passivated with, e.g., a nitride or oxide material, and such can be accomplished after metal evaporation and before lift-off processes. The nanopore can be produced at a selected site by, e.g., electron beam, or by other beam species or etching process that produces a selected nanopore dimension.

In fabrication of a graphene-based nanopore sensor including a nanowire structure on top of the graphene membrane, like the graphene-based nanopore sensor of FIGS. 7A-7B, first a membrane, such as a nitride membrane, is processed to form a micron-sized aperture in the membrane, e.g., by electron beam lithography or photolithography and reactive ion etching (RIE). Then a graphene sheet or piece is disposed on the nitride membrane, covering the aperture, to form a graphene membrane. The graphene sheet can be synthesized by CVD or other process, or produced by mechanical exfoliation, and transferred to the nitride membrane, over the nitride membrane aperture.

Electron beam lithography or photolithography can then be conducted with metal evaporation to define electrodes in the conventional manner on the nitride membrane. Dielectrophoresis or other suitable process can then be employed to align a nanowire, such as a silicon nanowire, on top of the graphene membrane at the location of the aperture in the nitride membrane. Electron beam lithography or photolithography can then be conducted with metal evaporation to define the source and drain contacts at ends of the SiNW. Thereafter, excessive graphene can be removed by electron beam lithography or photolithography and, e.g., UV-ozone stripper, oxygen plasma, or other suitable method to remove graphene from regions outside the intended graphene membrane location. Finally, a nanopore is produced through a site at the nanowire and the underlying graphene membrane by, e.g., an electron beam.

In fabrication of a graphene-based nanopore sensor including a graphene membrane that is on top of a nanowire FET structure, like the graphene-based nanopore sensor of FIGS. 8A-8B, a suitable structure can be employed for configuring the arrangement, e.g., with a silicon-on-insulator chip (SOI). In this example, an aperture is first formed through the backside thick silicon portion of the SOI chip, e.g., by $XF_2$ etching, stopping on the oxide layer, to form an oxide-silicon membrane. Then electron beam lithography or photolithography is employed to remove the oxide layer from the SOI chip in a smaller aperture region, producing a membrane of silicon from the thin silicon region of the SOI chip. This silicon membrane is then etched to form a nanowire of silicon, e.g., with electron beam lithography or photolithography and chemical etching or RIE. In one example, a dove-tail-shaped Si piece is formed as shown in FIG. 8B, aligned with the aperture in the oxide membrane of the SOI chip.

Electron beam lithography or photolithography can then be conducted with metal evaporation to define electrodes in the conventional manner on the oxide layer. Then a graphene sheet or piece is disposed on the oxide membrane, covering the aperture, to form a graphene membrane over the silicon nanowire. The graphene sheet can be synthesized by CVD or other process, or produced by mechanical exfoliation, and transferred to the oxide membrane, over the SiNW and oxide membrane aperture. It is recognized that because the graphene sheet is being overlaid on top of the patterned silicon layer, the graphene piece may not be flat. If leakage is a concern for this configuration, then a thin layer of, e.g., $SiO_x$ can be coated around the graphene edges to form a sealed edge condition.

Thereafter, excessive graphene can be removed by electron beam lithography or photolithography and, e.g., UV-ozone stripper, oxygen plasma, or other suitable method to remove graphene from regions outside the intended graphene membrane location. Finally, a nanopore is produced through a site at the overlying graphene and the silicon nanowire, e.g., by electron beam, in relation to the location of the most narrow Si geometry.

In fabrication of a graphene-based nanopore sensor like that depicted in FIG. 9A, first a membrane, such as a nitride membrane, is processed to form a micron-sized aperture in the membrane, e.g., by electron beam lithography or photolithography and reactive ion etching (RIE). Then a graphene sheet or piece is disposed on the nitride membrane, covering the aperture, to form a graphene membrane. The graphene sheet can be synthesized by CVD or other process, or produced by mechanical exfoliation, and transferred to the nitride membrane, over the nitride membrane aperture.

Electron beam lithography or photolithography can then be conducted with metal evaporation to define source and drain electrodes in the conventional manner on the graphene membrane. Thereafter, the graphene is patterned in a dovetail or other selected shape by electron beam lithography or photolithography and, e.g., UV-ozone stripper, oxygen plasma, or other suitable method to produce a narrow graphene region in the vicinity of the selected site for a nanopore. Finally, a nanopore is produced through the graphene membrane by, e.g., electron beam.

In fabrication of a SET-based nanopore sensor like that of FIG. 1F, any suitable membrane material, both electrically conductive and electrically insulating, can be employed. A nitride membrane structure or other structure can be employed, such as a graphene membrane or combination graphene-nitride membrane structure as-described above. If an electrically conducting membrane material is employed, it can be preferred to coat the material with an insulating layer, such as an oxide or nitride layer, on the side of the membrane on which the SET is to be formed. Electron beam lithography and metal evaporation techniques can then be employed to form the source and drain regions and the SET region out of a suitable metal. A nanopore can then be formed at the location of the SET in the manner given above. If an insulating layer is provided on an electrically conducting membrane material and the insulating layer coated the length of the nanopore through the membrane, then it can be preferred to remove that insulating material from the nanopore sidewall by, e.g., HF or other suitable etching, from the backside of the nanopore, to remove the insulator layer from the nanopore and from the adjacent vicinity of the nanopore.

In fabrication of a QPC arrangement like that of FIG. 1G with a nanopore, an SOI structure can be employed, removing the thick silicon layer in the manner described above, and then using electron beam lithography to define the top silicon layer structure in the QPC arrangement. The nanopore can then be formed through the membrane in the manner given above.

These example processes are not intended to be limiting and are provided as general examples of techniques for producing nanopore sensors. Any suitable membrane material and device material can be employed. For many applications it can be preferred that a nonconducting membrane material be employed in conjunction with a conducting nanowire material. The local electrical potential measurement method can be applied to any nanopore sensor and is not limited to a particular configuration or method for producing such configuration.

In each of these example processes, it is preferred that the dimensions of the nanopore be selected based on a selected ratio of the reservoir buffer solution concentrations, to achieve a desired electrical potential measurement in the manner described above, in conjunction with consideration for the species objects to be investigated with the nanopore sensor. The analytical expressions above can be employed to determine an optimum nanopore size for a given species to be detected by translocation through the nanopore, in concert with the other nanopore sensor parameters and operation, for enabling electrical potential measurement for nanopore sensing of the species.

This is particular important for maximizing the ability to distinguish between different species objects as nanopore translocation of the objects is conducted. For example, the graphene-based nanopore sensors described above are particularly attractive for sensing molecular species such as DNA and other biopolymer species because the graphene thickness is on the order of a DNA base extent. But because graphene is electrically gated on both sides of the graphene by the cis and trans reservoir solutions, and the electrical potential in the two reservoirs is opposite, the sum of electrical potentials that is indicated by the graphene potential measurement is smaller than that indicated by the implementation of a nanowire on one side of a membrane. But for a small nanopore, e.g., of about 1 nm in diameter, and with a sufficiently large ratio in buffer concentration between the cis and trans reservoirs, the sum of electrical potentials that is indicated by the graphene potential measurement is comparable to that of a nanowire nanopore sensor.

Based on Expression (8) above, it can be shown that a graphene nanopore sensor enables local potential measurements that distinguish between the A, G, C, and T DNA bases. The following table presents the cross-sectional areas of each of these DNA bases, including the DNA backbone, based on previous work as given, e.g., by M. Zwola et al. "Colloquium: Physical Approaches to DNA Sequencing and Detection," *Review of Modern Physics*, No. 80, pp. 141-165, 2008.

TABLE I

| Base + backbone | Cross-sect. Area (nm$^2$) |
|---|---|
| A | 0.4731 |
| G | 0.5786 |
| T | 0.5140 |
| C | 0.3932 |

Figure 11:
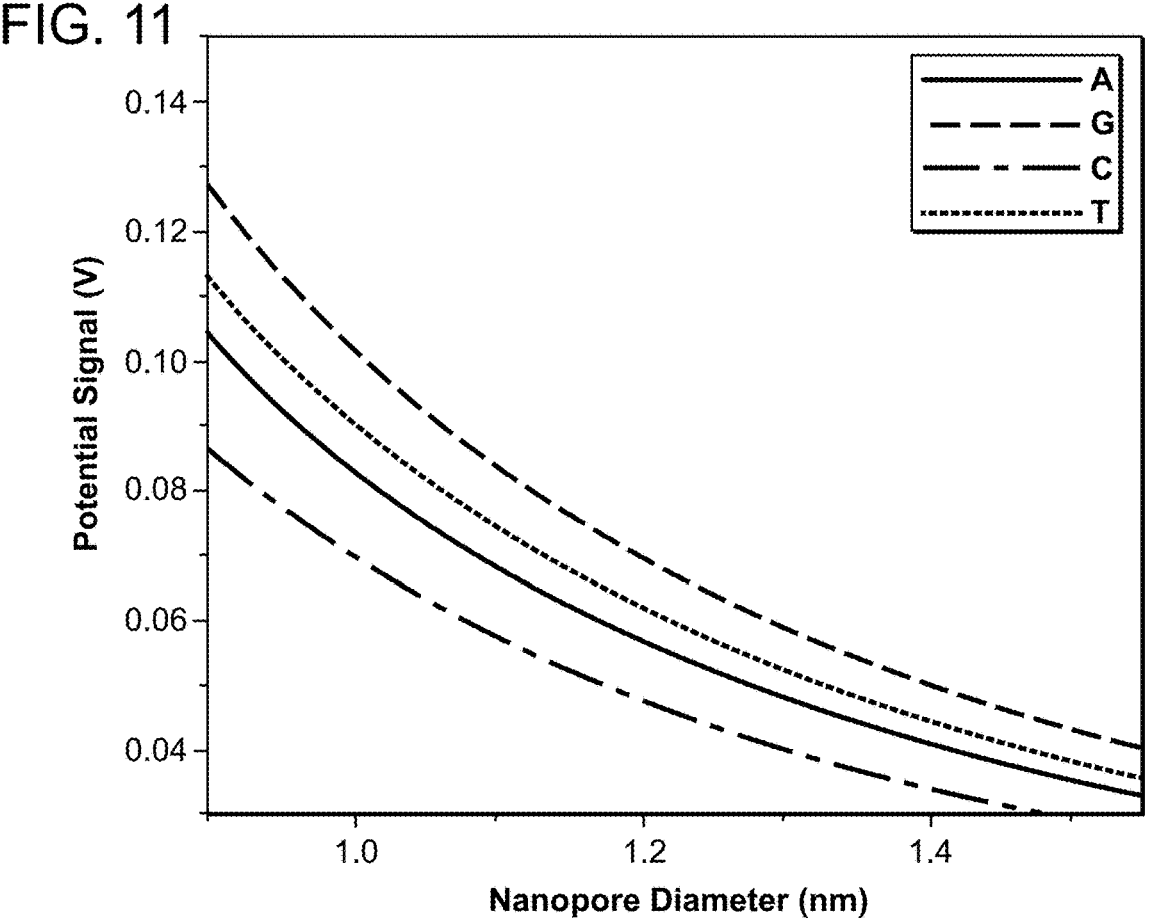
FIG. 11 is a plot of the electrical potential signal measured for each of the four DNA bases as a function of nanopore diameter for a nanopore sensor configured for local electrical potential measurement as the DNA bases translocate through the nanopore.

Given a graphene effective thickness in solution of about 0.6 nm and a concentration ratio of about 50:1 between the cis and trans reservoir buffer solution ionic concentrations, then the local potential measured by the nanopore sensor is as shown in the plots of FIG. 11 as a function of nanopore diameter. As shown in the plot, this demonstrates that the graphene-based nanopore sensor configured with differing cis and trans reservoir solution concentrations provides a local potential measurement signal difference of millivolts between each of the different bases, e.g., at least about 5 mV, and enables the ability to identify bases as the bases translocate through the graphene nanopore.

EXAMPLE I

Fabrication of a SiNW FET Device For Nanopore Sensing

SiNWs were synthesized using an Au-nanoparticle-catalyzed chemical vapor deposition (CVD) method. 30 nm-diameter gold nanoparticles (Ted Pella Inc.) were dispersed on a silicon wafer coated with a 600 nm-thick layer of silicon oxide (NOVA Electronic Materials Inc.). Boron-doped p-type SiNWs were synthesized at 435° C. and 30 Torr, with 2.4 standard cubic centimeters per minute (sccm) silane as a silicon source, 3 sccm diborane (100 ppm in helium) as a boron dopant source and 10 sccm argon as the carrier gas. The nominal doping ratio was 4000:1 (Si:B) and the growth time was 20 minutes. The resulting SiNWs were dissolved in ethanol by gentle sonication for ~10 seconds. Then the NW solution was deposited onto a 50 nm-thick, 100 µm×100 µm silicon nitride TEM membrane grid (SPI supplies). Electron beam lithography and evaporation of a 60 nm-thick layer of nickel were carried out to fabricate ~1 µm spaced-apart source and drain electrodes on the nanowire. A layer of thickness of about 75-100 nm of silicon nitride was then deposited by plasma enhanced CVD (NEXX Systems) on the chip immediately after metal evaporation, to passivate all electrodes.

Lift-off of the mask was then carried out to produce a nanowire on a nitride membrane having passivated source and drain electrodes. The structure was then annealed by a rapid thermal processor (HeatPulse 610, Total Fab Solutions) in forming gas at 380° C. for 135 seconds to shrink the nanowire channel to an extent less than about 200 nm. After conductivity testing of the resulting SiNW FET, the structure was cleaned by UV-ozone stripper (Samco International Inc.) at 150° C. for 25 minutes on each side. The structure was then loaded into a field emission transmission electron microscope (TEM) (JEOL 2010, 200 kV) and a nanopore of about 9 nm or 10 nm in extent was drilled by through the nanowire at a selected location by convergent high energy electron beam into one spot for approximately 2-5 minutes. The nanopore was sited at the edge of the nanowire, as depicted in the arrangement of FIG. 10B, whereby a substantial portion of the nanowire width was continuous.

EXAMPLE II

Sensitivity Profiling of a SiNW FET Device For Nanopore Sensing

The sensitivity of the SiNW FET sensor of the nanopore sensor was characterized by scanning gate microscopy (SGM). A SiNW FET device was fabricated in accordance with the method of Example I, here with ~2 µm long channel length to accommodate the limited spatial resolution of SGM. SGM was performed in a Nanoscope Ma Multi-Mode AFM (Digital Instruments Inc.) by recording the conductance of the nanowire as a function of the position of a −10 V biased conductive AFM tip (PPP-NCHPt, Nanosensors Inc.). The AFM tip was 20 nm above the surface during SGM recording.

Figure 12:
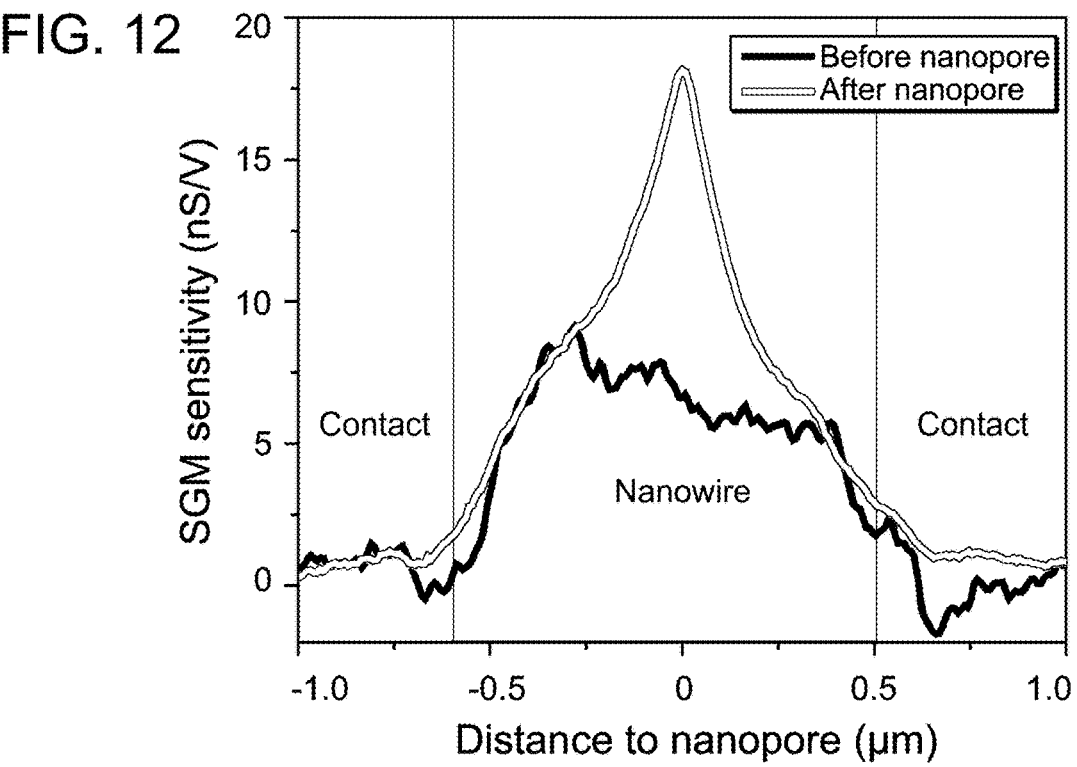
FIG. 12 is a plot of the sensitivity of a nanowire in a nanopore sensor configured for local electrical potential measurement before and after formation of a nanopore at the nanowire location.

Prior to formation of a nanopore at the nanowire site, an SGM profile was produced across the nanowire. Then a nanopore was formed at the edge of the nanowire in the arrangement depicted in FIG. 10B. With the nanopore present, the SGM profile of the nanowire was again produced. The SGM profile was determined by averaging the conductance over the apparent width (~100 nm) of the Si NW in a perpendicular direction using WSxM software. FIG. 12 is a plot of sensitivity, defined as conductance change divided by AFM tip gate voltage, along the nanowire before nanopore formation and after nanopore formation. It is clear that the sensitivity of the device is sharply localized and aligned with the nanopore. More importantly, the sensitivity of the nanopore region is also significantly enhanced compared to the sensitivity of the same region prior to nanopore formation.

EXAMPLE III

Cleaning and Assembly of a Nanowire-nanopore Device For Nanopore Sensing

The nanowire-nanopore assembly produced by the method of Example I above was cleaned by UV-ozone stripper (Samco International Inc.) at 150° C. for 25 minutes on each side after formation of the nanopore. This cleaning process is preferred to remove any possible carbon deposition on the structure. Then the structure was annealed in forming gas at 250° C.-350° C. for 30 seconds to recover the conductance of the nanowire. A further 25-minute room temperature UV-ozone cleaning was performed on each side of the structure to ensure hydrophilicity of the nanopore just before assembly.

To assemble the nanowire-nanopore structure with fluidic reservoirs for species translocation through the nanopore, PDMS chambers were sonicated first in DI water, then 70% ethanol and finally pure ethanol, each for ~30 minutes and then stored in pure ethanol. Just before assembly, PDMS chambers were baked in a clean glass petri dish at ~80° C. for ~2 hours to remove most of the absorbed ethanol.

A printed circuit board (PCB) chip carrier was produced for making electrical connection to the nanopore sensor, and was cleaned by Scotch-Brite (3M) to remove the copper surface oxide and any contaminants such as glue. The PCB was then sonicated in isopropyl alcohol and then in 70% ethanol, each for ~30 minutes. Gold solution electrodes were cleaned in piranha solution for ~1 hour just before assembly.

The cleaned nanowire-nanopore structure was glued into a ~250 μm-deep center pit of the PCB chip carrier using Kwik-Cast (World Precision Instruments, Inc.) silicone glue, with the device side surface approximately flush to the surface of the rest of PCB chip carrier. The source and drain electrical contacts of the device were wired to copper fingers on the chip carrier by wire bonding (West-Bond Inc.). The front PDMS chamber was formed of a piece of PDMS with a ~1.8 mm hole in the center, with a protrusion of ~0.5 mm around one side of the hole opening, for pressing against the nanopore membrane surface to ensure a tight seal. The PDMS chambers were mechanically clamped onto both sides of the chip carrier and Au electrodes were inserted through the PDMS reservoirs. The gold electrodes function as electrical connections for biasing the PDMS chamber solutions to produce a transmembrane voltage (TMV) for driving species translocation through the nanopore electrophoretically.

The trans chamber was selected as the reservoir in which potential measurements would be made for the nanopore sensor. Thus, the assembly was arranged with the membrane oriented such that the nanowire was located facing the trans reservoir. The trans chamber was filled with a solution having a concentration of ~10 mM buffer, with 10 mM KCl+0.1×TAE buffer: 4 mM tris-acetate and 0.1 mM EDTA solution. The cis chamber was accordingly filled with a higher ionic concentration solution to provide the requisite reservoir concentration ratio to provide a higher assess resistance at the site of local potential measurement, in the trans chamber. The cis chamber was filled with a solution of ~1 M buffer, as 1 M KCl+1×TAE buffer: 40 mM tris-acetate and 1 mM EDTA. Both solutions were auto-cleaved, degassed by house vacuum and filtered by 20 nm Anotop syringe filter (Whatman Ltd.) before use.

EXAMPLE IV

Nanopore Sensing of DNA Translocation Through the Nanopore

The nanowire-nanopore structure produced by the methods of the examples above and assembled with the solutions having buffer concentrations as prescribed by Example III was operated for sensing translocation of species objects, namely, double stranded DNA molecules of 1.4 nM pUC19 (dsDNA). Both the ionic current through the nanopore and the current from the nanowire FET device were measured.

The ionic current was amplified by an Axon Axopatch 200B patch-clamp amplifier (Molecular Devices, Inc.) with β=0.1 (1 nA convert to 100 mV) and 2 kHz bandwidth. The nanowire FET current was amplified by a DL 1211 current amplifier (DL Instruments) with a $10^6$ magnification (1 nA convert to 1 mV) and a 0.3 ms rise time. Both the transmembrane voltage (TMV) and voltage between the nanowire FET source and drain electrodes, $V_{sd}$, were acquired by an Axon Digidata 1440A digitizer (Molecular Devices, Inc.). Both nanopore ionic current and nanowire FET signals were fed into a 1440A digitizer, and recorded at 5 kHz by a computer. Operation of the nanopore sensor was carried out in a dark Faraday cage. To avoid 60 Hz noise that could be introduced by the electrical grounding from different instruments, the ground line was removed from all current amplifiers and all instruments (Amplifiers and digitizer) and the Faraday cage and were manually grounded to the building ground together.

Figure 13A:
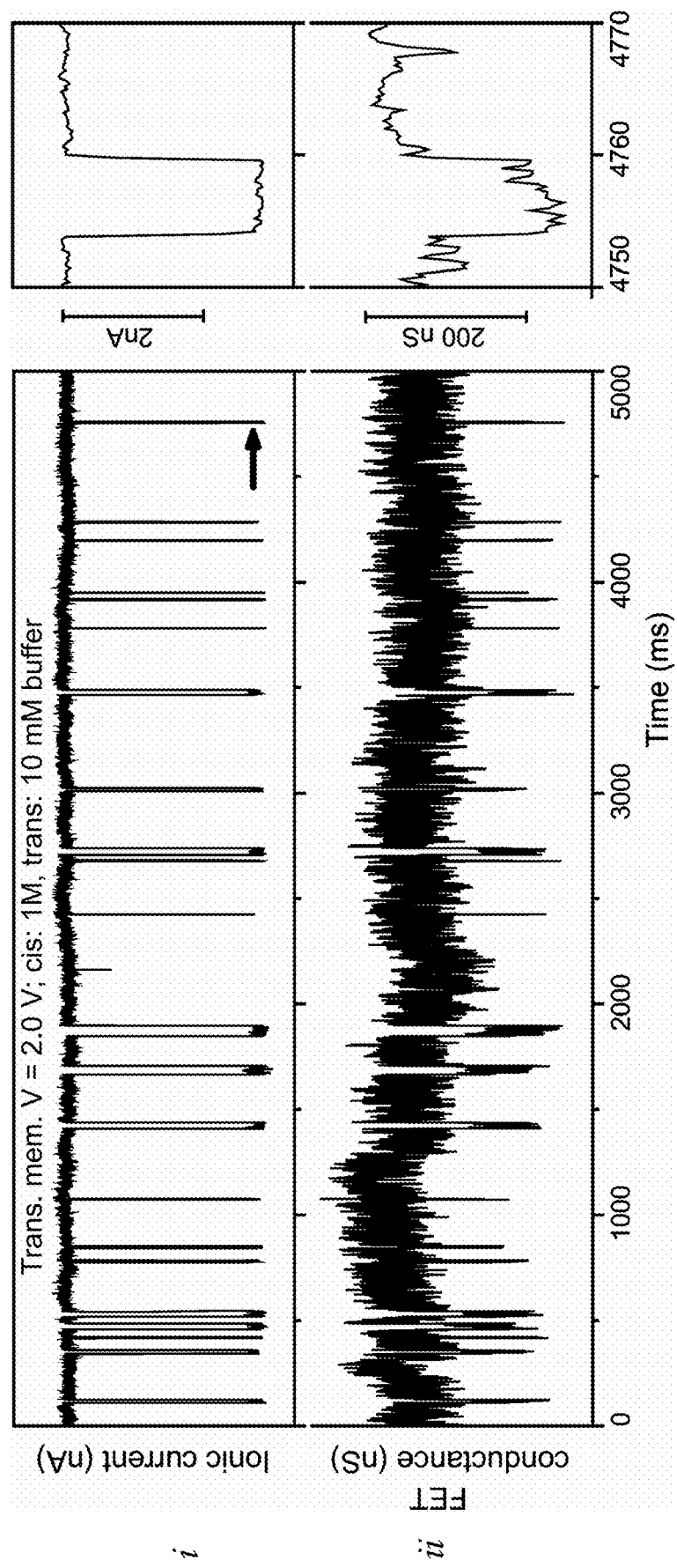
FIG. 13 A is a plot of i) measured ionic current through a nanopore and ii) measured nanowire FET conductance, respectively, as DNA translocates through a nanopore in a nanopore sensor configured for local electrical potential measurement, for a TMV of 2 V and 100:1 cis/trans reservoir solution concentration ratio, with a local potential measurement made in the trans reservoir.
FIG. 13B is a plot of i) measured ionic current through a nanopore and ii) measured nanowire FET conductance, respectively, as DNA translocates through a nanopore in a nanopore sensor configured for local electrical potential measurement, for a TMV of 2.4 V and 100:1 cis/trans reservoir solution concentration ratio, with a local potential measurement made in the trans reservoir.
FIG. 13C is a plot of i)measured ionic current through a nanopore and ii) measured nanowire FET conductance, respectively, as DNA translocates through a nanopore in a nanopore sensor configured for local electrical potential measurement, for a TMV of 0.6 V and 1:1 cis/trans reservoir solution concentration ratio, with a local potential measurement made in the trans reservoir.
Figure 13B:
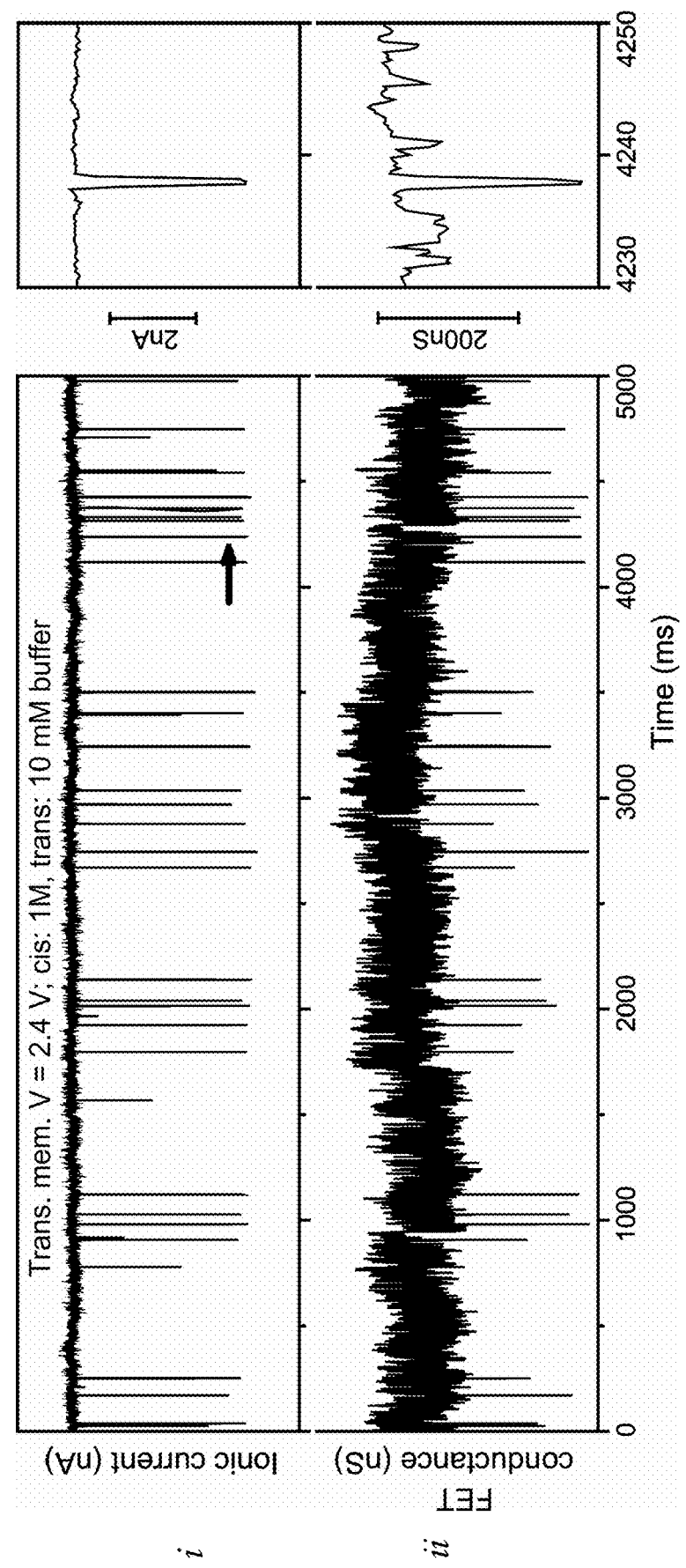

Upon introduction of the dsDNA into the cis reservoir, intermittent translocation events were recorded from the nanopore ionic current signal channel when the TMV reached ~2 V. For the nanowire FET signal channel, similar events were recorded in the conductance trace with almost perfect time correlation with the ionic current measurements. FIG. 13A is a plot, i, of the measured ionic current through the nanopore, and a plot, ii, of the measured nanowire FET conductance for a 2.0 V TMV. FIG. 13B is a plot, i, of the measured ionic current through the nanopore, and a plot, ii, of the measured nanowire FET conductance for a 2.4 V TMV. As the TMV was increased, the duration and frequency of translocation events measured by ionic current through the nanopore and measured by nanowire FET local potential sensing decreased and increased respectively. From the plots it is shown that the local potential measurement sensing method perfectly tracks the sensing by conventional ionic current measurement. The local potential measurement method thereby enables the determination of the time of and the duration of translocation of an object through the nanopore.

To directly compare the signal amplitudes of the FET local potential measurement signal and the nanopore ionic current measurement signal, the FET conductance signal of ~200 nS and baseline of ~24 μS was converted into a current by multiplying the signal by the 150 mV source-drain voltage. This calculation indicates that for ~2 nA of change in ionic current through the nanopore, with a ~12 nA baseline, there is produced an amplification to ~30 nA of FET current in the nanowire local potential measurement, with a ~3.6 μA baseline. Considering that current fabrication processes are not optimized for low noise devices and that a far higher signal-to-noise ratio has been demonstrated for SiNWs in general, the noise and signal-to-noise ratio of the nanowire FET itself is not be the fundamental limiting factor of this measurement.

EXAMPLE V

Local Potential Measurement Dependence on cis and trans Reservoir Buffer Concentration Difference To determine the impact of different ionic concentration fluids in the cis and trans reservoirs of the nanopore sensor, a nanowire-nanopore structure was configured following the procedure in Example III above, but here with both cis and trans chambers filled with 1 M KCl buffer instead of solutions having differing buffer concentrations. Operation of the nanopore sensor was then conducted with dsDNA provided in the trans reservoir, following the procedure of Example IV above, with a TMV of 0.6 V. The ionic current through the nanopore was measured, as was the local potential, via nanowire FET conductance in the manner of Example IV.

Figure 13C:
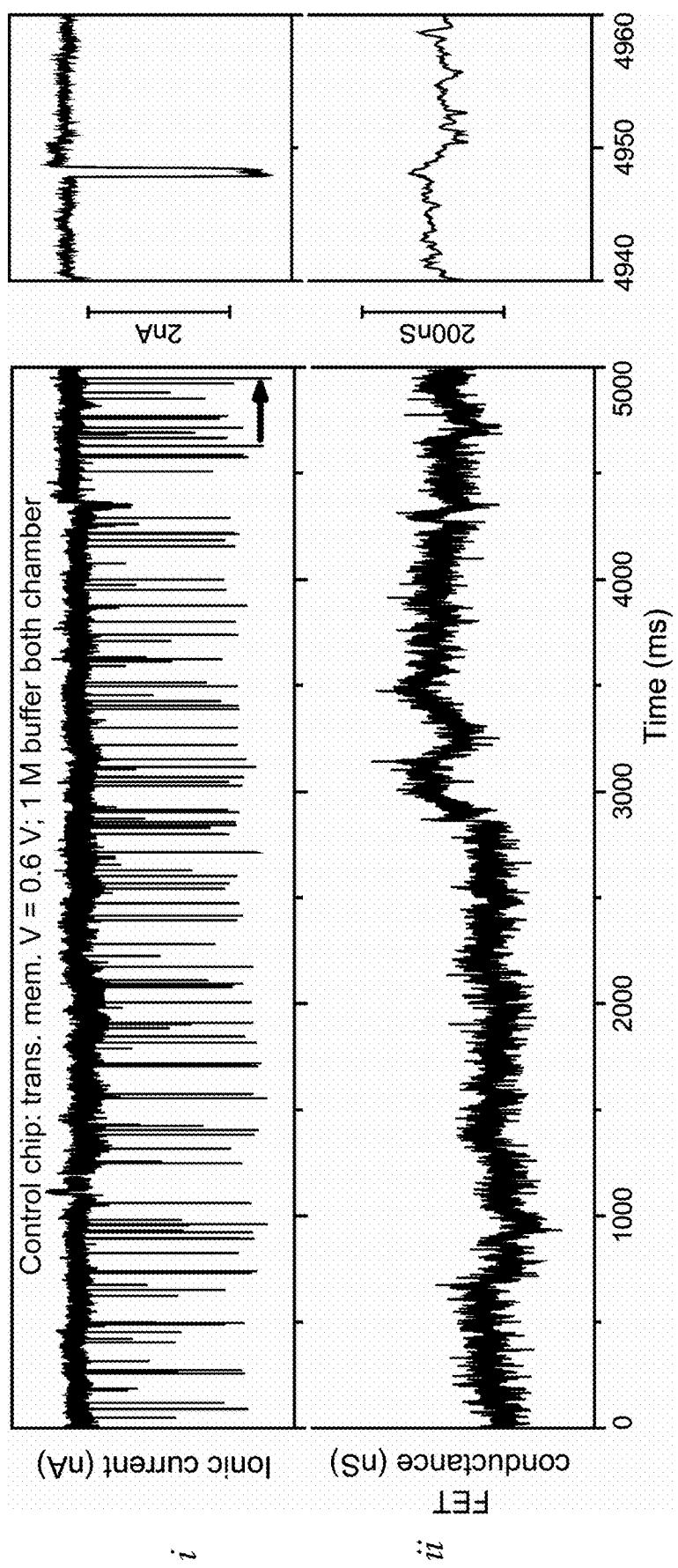

FIG. 13C provides plots of i, the measured ionic conductance and ii, the measured FET conductance. As shown in the plots, translocation events were sensed by changes in ionic current when the TMV reached 0.5-0.6 V but the simultaneously-recorded FET conductance change was negligible at that voltage. The reservoir solution concentration ratio is therefore understood to play an important role in the signal generation.

Under the balanced buffer solution concentration conditions (1 M/1 M) of this experiment, the nanopore solution resistance contributes the majority of the resistance of the nanopore sensor; thus, almost all of the TMV drops across the nanopore. The electrical potential in the vicinity of the nanowire sensor is accordingly for this condition very close to ground regardless of any change in the solution resistance of the nanopore and access resistances of the reservoirs due to blockade during species translocation. Under the non-balanced buffer conditions (10 mM/1 M) of Example IV above, the nanopore solution resistance and the trans chamber access resistance are comparable, while the access resistance of cis chamber is still negligible. Any change of the solution resistance in the nanopore and access resistance in the trans reservoir causes a corresponding redistribution of TMV and thus a change in the electrical potential in the vicinity of the nanopore at the trans chamber, and this potential change is what is easily detected by the local potential measurement of the nanopore sensor.

This example validates the discovery herein that local potential measurement nanopore sensing requires a difference in buffer solution concentration between the reservoirs of a nanopore sensor, and that the local potential measurement is to be conducted at the reservoir-side of the nanopore having a higher resistance, or correspondingly lower concentration. This condition is not applicable to nanopore sensors wherein the membrane is sufficiently thin to operate as a nanowire and to sense the potential on both sides of the membrane, as in graphene nanopore sensors in which a graphene nanowire provides an indication of a difference between potential on the two sides of a nanopore. In this case, a difference in buffer solution concentration is still preferable, but the local potential measurement is not strictly limited to one side or the other of the nanopore, given that the nanowire measurement inherently senses the potential on both sides of the membrane.

Note in the experiments above in which the reservoir solution concentrations were equal and were unequal required differing transmembrane voltages to initial translocation through the nanopore. For potential measurement in the trans reservoir, with equal solution concentrations, the electric field through the nanopore is constant, as shown in the plot of FIG. 3D. When the reservoir concentrations are different, e.g., the 100:1 concentration of the examples above, then the electric field through the nanopore is smaller on the cis reservoir-side of the nanopore. To produce the same electric field as that obtained with equal reservoir solution concentrations, the transmembrane voltage is required to be increased by about 4 times. This explains the data of the plots of FIGS. 12 and 13.

EXAMPLE VI

Multi-Channel Nanopore Sensing

Three nanowire nanopore sensors were constructed following the methods of the examples above. The three nanopore sensors were integrated with a common reservoir system, with a 1 M KCl buffer solution in the cis chamber and a 10 mM KCl buffer in the trans chamber. A transmembrane voltage of 3 V was employed, and 1.4 nM of pUC19 DNA was provided for translocation through the nanopores.

Figure 14:
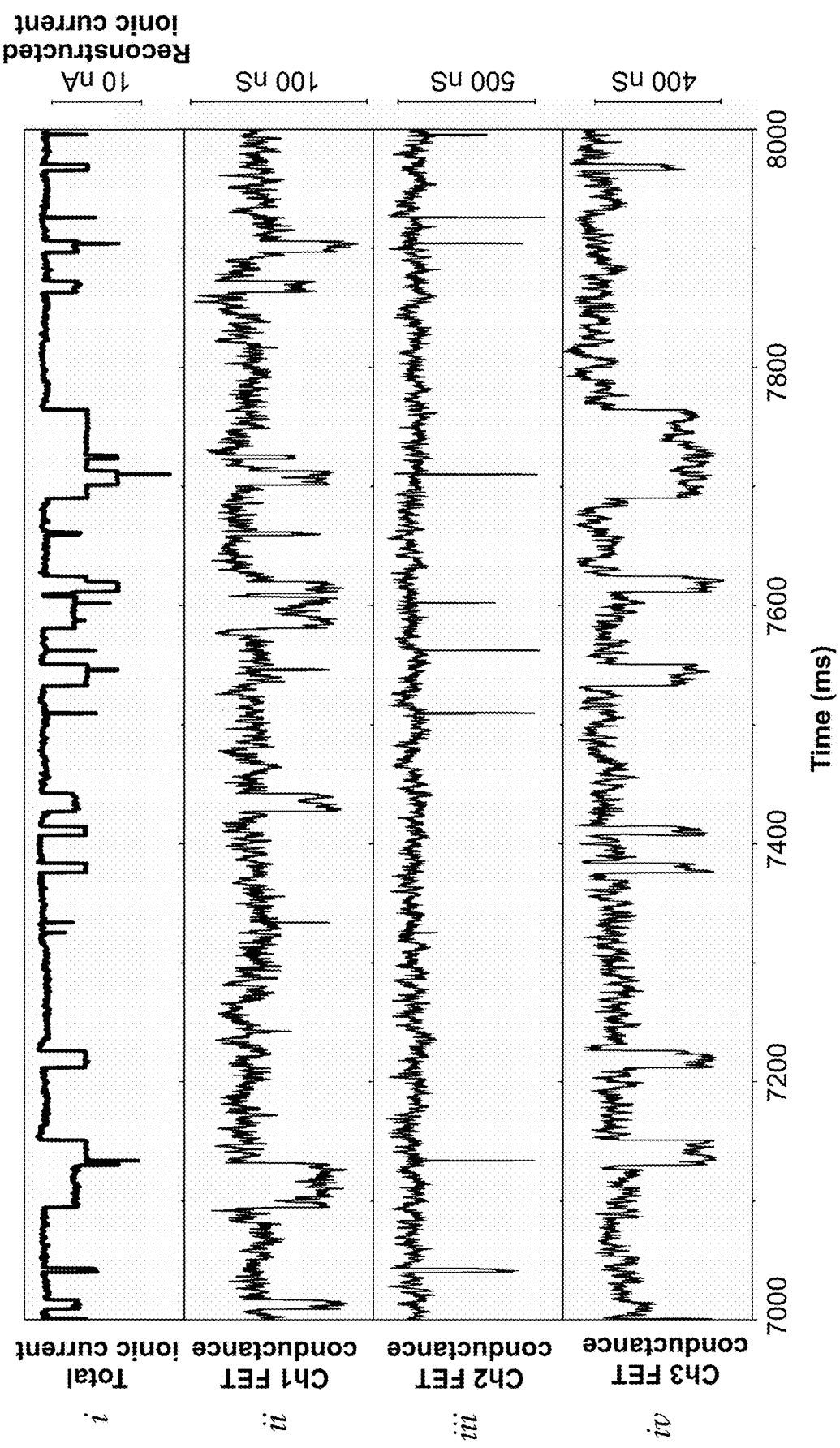
FIG. 14 is a plot of i) total ionic current measured through three nanopores sharing reservoirs, ii) measured nanowire FET conductance through the first of the nanopores, ii) measured nanowire FET conductance through the second of the nanopores, and ii) measured nanowire FET conductance through the third of the nanopores, respectively, as DNA translocates through the nanopores in the three sensors in a nanopore sensor configured for local electrical potential measurement.

FIG. 14 provides plots i-iv of total ionic current and the nanowire FET conductance of each of the three nanopore sensors, respectively, during DNA nanopore translocation operation. As shown in the plots, continuous translocation events are observed in all three nanopore sensors as well as the total ionic current channel. All nanopore sensors operated independently and every falling or rising edge apparent in the ionic current channel can be uniquely correlated to a corresponding edge in one of the three nanopore sensors. Using the falling and rising edge of signals from all three nanopore sensors to reconstruct the total ionic current trace, the reconstruction is nearly perfect for of all events. This nanopore operation demonstrates that a key advantage of the nanopore sensor is the large scale integration capability. Multiple independent nanopore sensors can be implemented without need for complex micro-fluidic systems.

With these examples and the preceding description, it is demonstrated that the nanopore sensor can provide sensing of species translocating through a nanopore and can discriminate between differing objects, such as DNA bases, as those objects translocate through the nanopore. The nanopore sensor is not limited to sensing of a particular species or class of species and can be employed for a wide range of applications. It is recognized that the nanopore sensor is particularly well-suited for sensing of biopolymer molecules that are provided for translocation through the nanopore. Such molecules include, e.g., nucleic acid chains such as DNA strands, an oligonucleotide or section of single-stranded DNA, nucleotides, nucleosides, a polypeptide or protein, amino acids in general, or other biological polymer chain. There is no particular limitation to the species object to be sensed by the nanopore sensor. With differing reservoir solution concentrations, it is demonstrated that the nanopore sensor can operate with reasonable bandwidth and sensitivity for discriminating DNA bases, and therefore enables DNA sequencing. It is recognized, that those skilled in the art may make various modifications and additions to the embodiments described above without departing from the spirit and scope of the present contribution to the art. Accordingly, it is to be understood that the protection sought to be afforded hereby should be deemed to extend to the subject matter claims and all equivalents thereof fairly within the scope of the invention.

We claim:

1. A multi-channel nanopore sensor comprising:
a plurality of independent nanopore sensors;
a first fluidic reservoir, common to all of the independent nanopore sensors in the plurality of independent nanopore sensors, with a first ionic solution of a first ionic concentration disposed in the first fluidic reservoir;
a second fluidic reservoir, common to all of the independent nanopore sensors in the plurality of independent nanopore sensors, with a second ionic solution of a second ionic concentration, different than the first ionic concentration, disposed in the second fluidic reservoir; and
each independent nanopore sensor in the plurality of independent nanopore sensors comprising:
a nanopore disposed in a support structure;
a fluidic connection between the first fluidic reservoir, common to all of the independent nanopore sensors in the plurality of independent nanopore sensors, and an inlet to the nanopore;
a fluidic connection between the second fluidic reservoir, common to all of the independent nanopore sensors in the plurality of independent nanopore sensors, and an outlet from the nanopore; and
an electrical transduction element disposed in contact with that ionic solution, of the first and second ionic solutions, which has a lower ionic concentration, the electrical transduction element being arranged at a site that produces in the electrical transduction element an electrical signal indicative of electrical potential local to that ionic solution having a lower ionic concentration.

2. The multi-channel nanopore sensor of claim 1 wherein the electrical transduction element of each independent nanopore sensor is disposed at one of the inlet to the nanopore and the outlet from the nanopore of that independent nanopore sensor, to indicate local electrical potential at one of the inlet to the nanopore and the outlet from the nanopore.

3. The multi-channel nanopore sensor of claim 1 wherein the electrical transduction element of each independent nanopore sensor comprises a plurality of electrical transduction elements, one transduction element disposed in the first ionic solution and one transduction element disposed in the second ionic solution, to indicate a difference in electrical potential local to the first ionic solution and electrical potential local to the second ionic solution, between the inlet to the nanopore and the outlet from the nanopore of that independent nanopore sensor.

4. The multi-channel nanopore sensor of claim 1 wherein the nanopore of each independent nanopore sensor has an electrical fluidic solution resistance and the reservoir of lower ionic concentration has an ionic concentration that provides in the reservoir of lower concentration an electrical reservoir access resistance that is of the same order of magnitude as the nanopore fluidic solution resistance and that is at least an order of magnitude greater than a reservoir access resistance of the reservoir of higher ionic concentration.

5. The multi-channel nanopore sensor of claim 1 wherein one of the first ionic concentration and the second ionic concentration is at least about 20 times greater than the other ionic concentration.

6. The multi-channel nanopore sensor of claim 1 wherein one of the first ionic concentration and the second ionic concentration is at least about 50 times greater than the other ionic concentration.

7. The multi-channel nanopore sensor of claim 1 wherein one of the first ionic concentration and the second ionic concentrations is at least about 100 times greater than the other ionic concentration.

8. The multi-channel nanopore sensor of claim 1 wherein a difference between the first ionic concentration, of the first fluidic reservoir, and the second ionic concentration, of the second fluidic reservoir, positions a local electrical potential signal decay length, measured from one of the inlet to the nanopore and the outlet from the nanopore of each independent nanopore sensor, that is at least about 5 nm.

9. The multi-channel nanopore sensor of claim 1 wherein a difference between the ionic concentration, of the first fluidic reservoir, and the second ionic concentration, of the second fluidic reservoir, imposes a local electrical potential signal, produced in the transduction element, that is characterized by a bandwidth of at least about 50 MHz.

10. The multi-channel nanopore sensor of claim 1 wherein the nanopore of each independent nanopore sensor is characterized by a diameter that is between about 1 nm and about 5 nm.

11. The multi-channel nanopore sensor of claim 1 wherein the nanopore of each independent nanopore sensor is characterized by a diameter that is between about 1 nm and about 2 nm.

12. The multi-channel nanopore sensor of claim 1 wherein the electrical transduction element of each independent nanopore sensor is disposed on the nanopore support structure at one of the inlet to the nanopore and the outlet from the nanopore of each independent nanopore sensor.

13. The multi-channel nanopore sensor of claim 1 wherein the electrical transduction element of each independent nanopore sensor comprises an electrical device or device region.

14. The multi-channel nanopore sensor of claim 1 wherein the electrical transduction element of each independent nanopore sensor comprises an electrical circuit.

15. The multi-channel nanopore sensor of claim 1 wherein the electrical transduction element of each independent nanopore sensor comprises a transistor.

16. The multi-channel nanopore sensor of claim 15 wherein the electrical transduction element of each independent nanopore sensor comprises a single electron transistor.

17. The multi-channel nanopore sensor of claim 15 wherein the transistor of each independent nanopore sensor is disposed on the nanopore support structure.

18. The multi-channel nanopore sensor of claim 15 wherein the electrical transduction element of each independent nanopore sensor comprises a field effect transistor.

19. The multi-channel nanopore sensor of claim 18 wherein the field effect transistor of each independent nanopore sensor includes an electronic conduction channel that is disposed at the nanopore of that independent nanopore sensor.

20. The multi-channel nanopore sensor of claim 18 wherein the electrical transduction element of each independent nanopore sensor comprises a nanowire field effect transistor.

21. The multi-channel nanopore sensor of claim 20 wherein the nanowire field effect transistor of each independent nanopore sensor comprises a silicon nanowire.

22. The multi-channel nanopore sensor of claim 1 wherein the support structure in which the nanopore of each independent nanopore sensor is disposed comprises a membrane.

23. The multi-channel nanopore sensor of claim 22 wherein the electrical transduction element of each independent nanopore sensor comprises a nanowire disposed on the membrane at a location of one of the inlet to the nanopore and the outlet from the nanopore of that independent nanopore sensor.

24. The multi-channel nanopore sensor of claim 1 wherein the support structure in which the nanopore of each independent nanopore sensor is disposed comprises a suspended layer of graphene.

25. The multi-channel nanopore sensor of claim 1 wherein the electrical transduction element of each independent nanopore sensor comprises a graphene layer in which the nanopore is disposed.

26. The multi-channel nanopore sensor of claim 1 wherein the support structure of each independent nanopore sensor comprises a solid state material.

27. The multi-channel nanopore sensor of claim 1 wherein the support structure of each independent nanopore sensor comprises a biological material.

28. The multi-channel nanopore sensor of claim 1 wherein the support structure of each independent nanopore sensor comprises a lipid bilayer and wherein the transduction element of each independent nanopore sensor comprises a region of the lipid bilayer that includes fluorescent dye which changes fluorescence in response to changes in local electrical potential.

29. The multi-channel nanopore sensor of claim 1 wherein the nanopore of each independent nanopore sensor comprises a biological nanopore.

30. The multi-channel nanopore sensor of claim 1 wherein the nanopore of each independent nanopore sensor comprises a protein nanopore.

31. The multi-channel nanopore sensor of claim 1 further comprising an electrical connection, between the first ionic solution and the second ionic solution, that applies a voltage bias between the inlet to the nanopore of each independent nanopore sensor and the outlet from the nanopore of each independent nanopore sensor to electrophoretically drive objects through the nanopore of each independent nanopore sensor.

32. The multi-channel nanopore sensor of claim 31 wherein one of the first ionic concentration and the second ionic concentration is at least about 100 times greater than the other ionic concentration, and further comprising an electrical circuit connected to the transduction element of each independent nanopore sensor and configured to produce a different electrical signal for translocation of each of A, T, G, and C DNA bases through a nanopore in one of the independent nanopore sensors, with a difference of at least 5 mV between different electrical signals.

33. The multi-channel nanopore sensor of claim 1 wherein the electrical transduction element of each independent nanopore sensor is arranged at a site that produces an electrical signal indicative of electrical potential local to that ionic solution, of the first and second ionic solutions, having a lower ionic concentration, in response to a molecule translocating through the nanopore of that independent nanopore sensor in the plurality of independent nanopore sensors.

34. The multi-channel nanopore sensor of claim 1 wherein the electrical transduction element of each independent nanopore sensor is arranged at a site that produces an electrical signal indicative of electrical potential local to that ionic solution, of the first and second ionic solutions, having a lower ionic concentration, in response to translocation through the nanopore, of that independent nanopore sensor, of at least one object selected from DNA, DNA fragments, RNA, RNA fragments, nucleotides, nucleosides, oligonucleotides, proteins, polypeptides, and amino acids.

35. The multi-channel nanopore sensor of claim 1 wherein the electrical transduction element of each independent nanopore sensor is arranged at a site that produces an electrical signal indicative of electrical potential local to that ionic solution, of the first ionic solution and the second ionic solution, having a lower ionic concentration, in response to translocation through the nanopore of that independent nanopore sensor of a corresponding one of each of A, T, G, and C DNA bases.

36. The multi-channel nanopore sensor of claim 1 further comprising signal processing electronics connected to the transduction element of each independent nanopore sensor and configured to process indicated electrical potential as a function of time to determine time of translocation and duration of translocation of objects through the nanopore of each independent nanopore sensor in the plurality of independent nanopore sensors.

37. The multi-channel nanopore sensor of claim 1 further comprising signal processing electronics connected to the transduction element of each independent nanopore sensor and configured to process indicated electrical potential as a function of time to identify objects as objects translocate through the nanopore of each independent nanopore sensor in the plurality of independent nanopore sensors.

38. The multi-channel nanopore sensor of claim 1 further comprising signal processing electronics connected to the transduction element of each independent nanopore sensor configured to process indicated electrical potential as a function of time to identify DNA bases as DNA bases translocate through the nanopore of each independent nanopore sensor in the plurality of independent nanopore sensors.

39. A multi-channel nanopore sensor comprising:
a plurality of independent nanopore sensors;
a first fluidic reservoir, common to all of the independent nanopore sensors in the plurality of independent nanopore sensors, with a first ionic solution of a first ionic concentration disposed in the first fluidic reservoir;
a second fluidic reservoir, common to all of the independent nanopore sensors in the plurality of independent nanopore sensors, with a second ionic solution of a second ionic concentration, different than the first ionic concentration, disposed in the second fluidic reservoir; and
each independent nanopore sensor in the plurality of independent nanopore sensors comprising:
a biological nanopore;
a fluidic connection between the first fluidic reservoir, common to all of the independent nanopore sensors in the plurality of independent nanopore sensors, and an inlet to the biological nanopore;
a fluidic connection between the second fluidic reservoir, common to all of the independent nanopore sensors in the plurality of independent nanopore sensors, and an outlet from the biological nanopore; and
an electrical transduction element disposed in contact with that ionic solution, of the first and second ionic solutions, which has a lower ionic concentration, the electrical transduction element being arranged at a site that produces in the electrical transduction element an electrical signal indicative of electrical potential local to that ionic solution having a lower ionic concentration.

* * * * *